United States Patent
Shaw et al.

(10) Patent No.: US 9,834,771 B2
(45) Date of Patent: Dec. 5, 2017

(54) APTAMERS AGAINST GLIOMA CELLS

(71) Applicant: University of Central Lancashire, Preston (GB)

(72) Inventors: Lisa Shaw, Preston (GB); Clare Lawrence, Preston (GB); Jane Alder, Preston (GB)

(73) Assignee: University of Central Lancashire (GB)

( * ) Notice: Subject to any disclaimer, the term of this patent is extended or adjusted under 35 U.S.C. 154(b) by 0 days.

(21) Appl. No.: 14/903,973

(22) PCT Filed: Jul. 9, 2014

(86) PCT No.: PCT/GB2014/000279
§ 371 (c)(1),
(2) Date: Jan. 8, 2016

(87) PCT Pub. No.: WO2015/004412
PCT Pub. Date: Jan. 15, 2015

(65) Prior Publication Data
US 2016/0152982 A1    Jun. 2, 2016

(30) Foreign Application Priority Data

Jul. 9, 2013 (GB) .................................. 1312340.1
Dec. 12, 2013 (GB) .................................. 1322021.5

(51) Int. Cl.
| | | |
|---|---|---|
| A61K 31/70 | (2006.01) |
| C07H 21/02 | (2006.01) |
| C07H 21/04 | (2006.01) |
| C12N 15/115 | (2010.01) |
| A61K 45/06 | (2006.01) |
| A61K 31/7105 | (2006.01) |
| A61K 49/00 | (2006.01) |
| A61K 51/04 | (2006.01) |
| C12N 5/00 | (2006.01) |

(52) U.S. Cl.
CPC ........ *C12N 15/115* (2013.01); *A61K 31/7105* (2013.01); *A61K 45/06* (2013.01); *A61K 49/0054* (2013.01); *A61K 51/0491* (2013.01); *C12N 2310/16* (2013.01); *C12N 2310/3519* (2013.01)

(58) Field of Classification Search
None
See application file for complete search history.

(56) References Cited

U.S. PATENT DOCUMENTS

| | | | | |
|---|---|---|---|---|
| 2005/0026201 A1* | 2/2005 | Matsuyama | ......... | C12N 15/113 435/6.13 |
| 2010/0209440 A1* | 8/2010 | Shankar | ................ | C12N 15/111 424/178.1 |
| 2011/0166213 A1* | 7/2011 | De Franciscis | ....... | C12N 15/111 514/44 R |
| 2011/0197292 A1* | 8/2011 | Sullenger | .............. | C12N 15/111 800/13 |

FOREIGN PATENT DOCUMENTS

| | | |
|---|---|---|
| EP | 2159286 A1 | 3/2010 |
| WO | 2008019142 A2 | 2/2008 |

OTHER PUBLICATIONS

Cherchia. "Differential SELEX in Human Glioma Cell Lines." PLoS One. 4.11(2009):e7971.
EBI Accession No. GSN:AXW67181, Apr. 29, 2010.
EBI Accession No. GSN:AXW67182, Apr. 29, 2010.
EBI Accession No. GSN:AXW67194, Apr. 29, 2010.
Kang et al. "Selection of DNA Aptamers against Glioblastoma Cells with High Affinity and Specificity." PLOS ONE. 7.10(2012):e42731.
Zaunbrecher et al. "Enhancement of Extra Chromosomal Recombination in Somatic Cells by Affecting the Ratio of Homologous Recombination (HR) to Non-Homologous End Joining (NHEJ)." Animal Biotechnol. 19.1(2008):6-21.

* cited by examiner

*Primary Examiner* — Sean McGarry
(74) *Attorney, Agent, or Firm* — Burns & Levinson LLP; Shawn P. Foley

(57) ABSTRACT

Provided are aptamers able to bind to ligands associated with cancer cells. The ligands may particularly be associated with brain cancers, such as gliomas. The aptamers may be used therapeutically for the prevention and/or treatment of such cancers. Aptamers may be associated with anti-cancer agents, or with detection moieties. Also provided are pharmaceutical compositions and methods of treatment employing such aptamers.

29 Claims, 26 Drawing Sheets

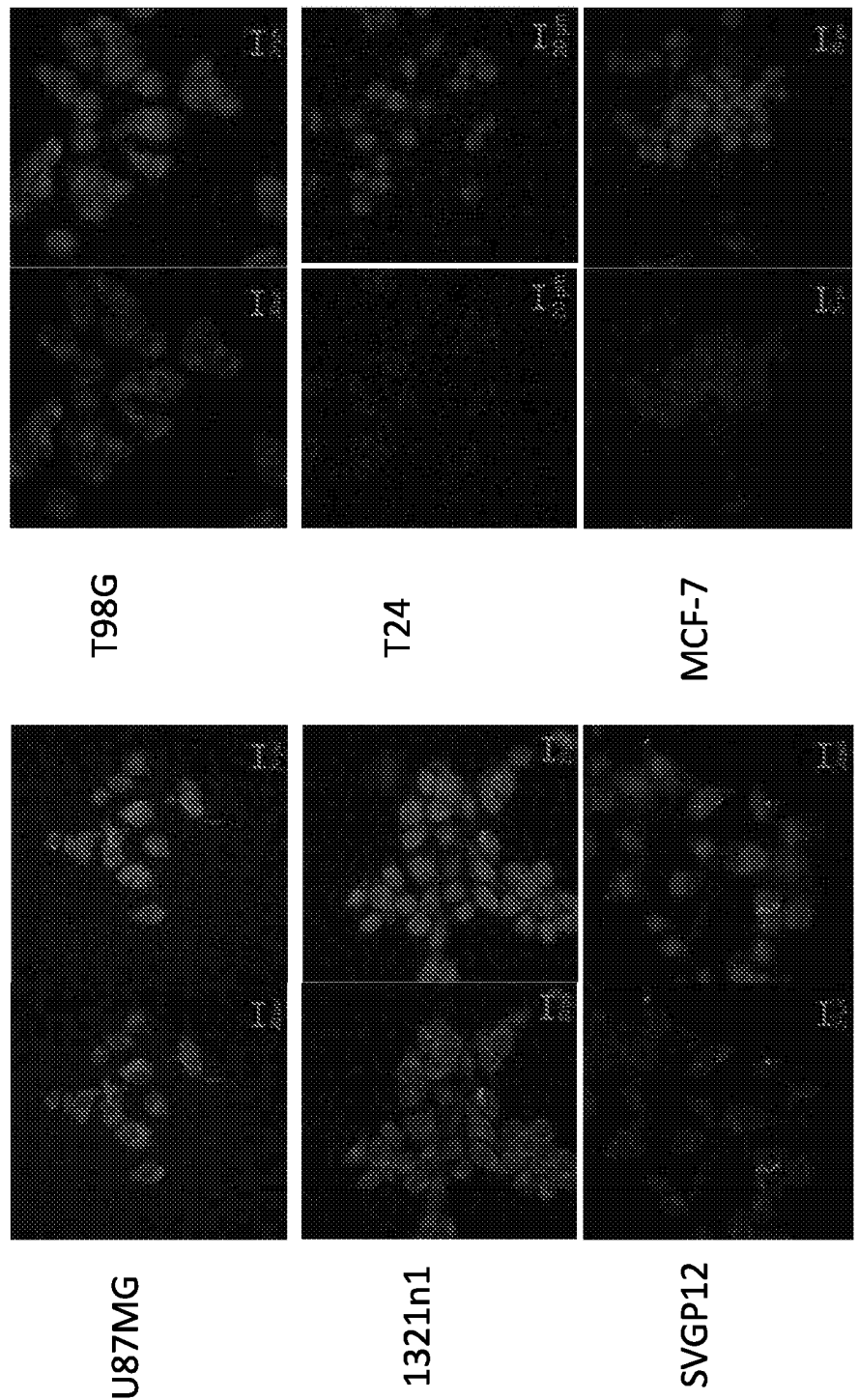

SEQUENCE LISTING

<160> NUMBER OF SEQ ID NOS: 12

<210> SEQ ID NO 1
<211> LENGTH: 45
<212> TYPE: DNA
<213> ORGANISM: Artificial Sequence
<220> FEATURE:
<223> OTHER INFORMATION: Aptamer also designated SA44 or GL44

<400> SEQUENCE: 1
acguuacucu ugcaacaccc aaacuuuaau agccucuuau aguuc        45

<210> SEQ ID NO 2
<211> LENGTH: 43
<212> TYPE: DNA
<213> ORGANISM: Artificial Sequence
<220> FEATURE:
<223> OTHER INFORMATION: Aptamer also designated SA43 or GL43

<400> SEQUENCE: 2
acguuacucu ugcaacacaa acuuuaauag ccucuuauag uuc           43

<210> SEQ ID NO 3
<211> LENGTH: 43
<212> TYPE: DNA
<213> ORGANISM: Artificial Sequence
<220> FEATURE:
<223> OTHER INFORMATION: Aptamer also designated SA56 or GL56

<400> SEQUENCE: 3
ugauuuugca gcacuucuug uuaucuuaac gaacuguuga uga           43

<210> SEQ ID NO 4
<211> LENGTH: 45
<212> TYPE: DNA
<213> ORGANISM: Artificial Sequence
<220> FEATURE:
<223> OTHER INFORMATION: Aptamer also desginated CL44

<400> SEQUENCE: 4
ggaaaauuau acccuccauu aaauccacca uuaccacacc cuuua        45

<210> SEQ ID NO 5
<211> LENGTH: 50
<212> TYPE: DNA
<213> ORGANISM: Artificial Sequence
<220> FEATURE:
<223> OTHER INFORMATION: Aptamer also designated U87TDM1

<400> SEQUENCE: 5
gtagggactt agctctcacc gtatggcatg cgtagtactg agagtgtggg     50

<210> SEQ ID NO 6
<211> LENGTH: 50
<212> TYPE: DNA
<213> ORGANISM: Artificial Sequence
<220> FEATURE:
<223> OTHER INFORMATION: Aptamer also designated U87TDM2

<400> SEQUENCE: 6
cactccaaaa ctcacctgaa ctgtaatagg ggatgtgtgc tacactatcg    50

<210> SEQ ID NO 7
<211> LENGTH: 50
<212> TYPE: DNA
<213> ORGANISM: Artificial Sequence

```
<220> FEATURE:
<223> OTHER INFORMATION: Aptamer also designated U87TDM3

<400> SEQUENCE: 7
ggcacattcc gacacgggtt ggcggtttgg gattgatgaa ctggcagttg            50

<210> SEQ ID NO 8
<211> LENGTH: 49
<212> TYPE: DNA
<213> ORGANISM: Artificial Sequence
<220> FEATURE:
<223> OTHER INFORMATION: Aptamer also designated U87TDM6

<400> SEQUENCE: 8
gcgtatcgac cacaaacaat aaggttacct gatctagtac gggttgttt             49

<210> SEQ ID NO 9
<211> LENGTH: 50
<212> TYPE: DNA
<213> ORGANISM: Artificial Sequence
<220> FEATURE:
<223> OTHER INFORMATION: Aptamer also designated U87TDM7

<400> SEQUENCE: 9
gcggcagctg tgcccgtgct gcgtctagac tcgtgatgag aaggagggct            50

<210> SEQ ID NO 10
<211> LENGTH: 50
<212> TYPE: DNA
<213> ORGANISM: Artificial Sequence
<220> FEATURE:
<223> OTHER INFORMATION: Aptamer also designated U87TDM9

<400> SEQUENCE: 10
cgctcattcg tggatgatta atgcggagcg tggtgggaag cgggcagcgg            50

<210> SEQ ID NO 11
<211> LENGTH: 50
<212> TYPE: DNA
<213> ORGANISM: Artificial Sequence
<220> FEATURE:
<223> OTHER INFORMATION: Aptamer also designated U87TDM10

<400> SEQUENCE: 11
ccgctagtgg gcggacgatg cgtgggatag gggggcgaat tgggggattt            50

<210> SEQ ID NO 12
<211> LENGTH: 43
<212> TYPE: DNA
<213> ORGANISM: Artificial Sequence
<220> FEATURE:
<223> OTHER INFORMATION: Randomly generated sequence designated neg
      aptamer

<400> SEQUENCE: 12
ccguuaauua ggcccuuaaa uggcauaaaa uuugaaaggg aau                   43
```

APTAMERS AGAINST GLIOMA CELLS

CROSS-REFERENCE TO RELATED APPLICATIONS

The present application is a national phase entry under 35 U.S.C. §371 of International Application No. PCT/GB2014/000279 filed Jul. 9, 2014, published in English, which claims priority from United Kingdom Application No. 1312340.1, filed Jul. 9, 2013, and United Kingdom Application No. 1322021.5, filed Dec. 12, 2013, all of which are incorporated herein by reference.

INCORPORATION BY REFERENCE OF MATERIAL IN ASCII TEXT FILE

This application incorporates by reference the Sequence Listing contained in the following ASCII text file:

a) File name: SequenceListing.txt; created Feb. 14, 2016, 3 KB in size.

The present invention relates to aptamers, ligand-binding fragments of aptamers, and oligonucleotides. The invention also relates to the uses of these agents in the prevention and/or treatments of cancers, and diagnosis of cancers. The agents and methods disclosed are particularly useful in brain cancers such as gliomas.

INTRODUCTION

In 2010, there were 9,156 new cases of brain cancer in the UK alone (Cancer Research UK). Worldwide it is estimated that there are 445,000 new cases of brain cancer every year (Cancer Research UK). On average a prognosis of less than 5% survival beyond 5 years is observed for patients diagnosed with GBM (WHO grade IV) (Ohgaki and Kleihues, 2005; Schwartzbaum et al., 2006). As the population grows every year, so the incidence of brain cancer will follow, highlighting the need for improved diagnosis, prognosis and prediction of response to treatment. This invention has the potential to fulfil this need both in the UK and worldwide.

The aim of brain tumour surgery is to maximise the removal of neoplastic tissues and minimise collateral damage to the surrounding normal brain tissues as well as vascular structures (Thoman et al., 2006). Several studies have demonstrated that current therapies are limited by ineffective early diagnosis, insufficient drug concentrations reaching the tumour, drug toxicity and poor therapeutic monitoring (Li et al., 2009; Jiang et al., 2010; Esposito et al., 2011). It has always been a challenge for scientific researchers including the pharmaceutical industry to discover a drug which can only kill cancer cells while sparing normal cells. Targeted drug delivery for cancer demands a homing device which can specifically carry the drug to cancer cells due to the over expression of a receptor for the homing device. Molecular targeting has been one of the novel approaches in the diagnosis and treatment of glioma. This approach is based on identifying a population of glioma cancer cells, which may express a unique receptor or antigen to be used as a targeting molecule for therapeutic purposes (Cibiel et al., 2011; Meyer et al., 2011).

A number of biological delivery systems have been used selectively to target imaging probes to tumour cells with aptamers and monoclonal antibodies receiving significant attention in the literature (Heilig, 2004; Shangguan et al., 2008; Cibiel et al., 2011). The project will utilise aptamers which are small and highly structured single stranded DNA or RNA molecules as ideal targeting agents because of their highly defined three dimensional structure which helps them to bind with high affinity to their targeted molecules with nanomolar affinities and high specificity (Cerchia et al., 2009; Bayrac et al., 2011).

According to a first aspect of the invention there is provided an aptamer comprising a nucleic acid sequence selected from the group consisting of: SEQ ID NO: 1; SEQ ID NO: 2; SEQ ID NO: 3; SEQ ID NO: 6; SEQ ID NO: 7; SEQ ID NO: 8; SEQ ID NO: 9; SEQ ID NO: 10; and SEQ ID NO: 11, or a ligand-binding fragment of such an aptamer.

The aptamers in accordance with the first aspect of the invention have been selected on the basis of their capacity to bind to ligands associated with cancer cells. This binding profile means that the aptamers of the invention have utility in a number of applications, including, but not limited to: therapeutic uses; diagnostic uses; and research uses. More details regarding these uses are set out elsewhere in the present disclosure.

Aptamers of the invention, as exemplified by the aptamer of SEQ ID NO: 2, demonstrate the surprising, and beneficial, property of being able to cross the blood-brain-barrier. This property is advantageous in that the blood-brain-barrier may otherwise constitute a considerable obstacle to agents (such as therapeutic or imagining agents) administered to the body being able to access sites within the brain where cancer, such as glioma, is present. It is surprising in that previously published results have indicated that in order for aptamers to cross the blood-brain-barrier it is necessary to conjugate them with targeting moieties. The ability of the aptamers of the invention to cross the blood-brain-barrier without addition of such targeting moieties is thus an unexpected advantage.

It will be appreciated that some variation is likely to be able to be made to the aptamers of the first aspect of the invention, or ligand-binding fragments thereof, without losing the essential functions of these aptamers and fragments. Accordingly, the invention also provides oligonucleotides sharing at least 75%, at least 80%, at least 85%, at least 90%, at least 95%, at least 96%, at least 97%, at least 98% or at least 99% sequence identity with any one of SEQ ID NOS: 1 to 3 or 6 to 11, wherein the oligonucleotide retains the same binding profile as the aptamer in question. For the sake of brevity, and except for where the context requires otherwise, references in the present disclosure to "aptamers of the invention" should also be taken as encompassing oligonucleotides based upon such aptamers.

Binding profiles of oligonucleotides and the ligand-binding nature of fragments of aptamers of the invention can readily be determined, for example using the methods, such as flow cytometry techniques, described in the Experimental Results section. Other suitable techniques by which binding profiles and ligand-binding can be experimentally established in respect of oligonucleotides or fragments of the aptamers of the first aspect of the invention will be apparent to those skilled in the art.

Without detracting from the considerations above, regarding variants based upon the aptamer sequences disclosed herein, in a suitable embodiment, an aptamer of the first aspect of the invention may consist of a nucleic acid sequence selected from the group consisting of: SEQ ID NO: 1; SEQ ID NO: 2; SEQ ID NO: 3; SEQ ID NO: 6; SEQ ID NO: 7; SEQ ID NO: 8; SEQ ID NO: 9; SEQ ID NO: 10; and SEQ ID NO: 11.

The ability of aptamers of the invention, or ligand binding fragments thereof, to bind to ligands associated with cancer cells make these agents highly suitable for use in therapeutic applications. The skilled person will appreciate that the ability of the aptamers of the invention to bind to ligands associated with cancer cells makes these aptamers very suitable for use in therapeutic application where it is wished to target anti-cancer agents to tumours.

Merely by way of example, many therapeutic strategies have been devised in which agents that bind to elements of cancer cells (for example markers expressed on the surface of such cancer cells) are used to target the delivery of therapeutic payloads. It will be appreciated that the aptamers of the present invention are well suited to such use.

Such embodiments may make therapeutic use of an aptamer of the invention, or a ligand-binding fragment thereof, in association with an anti-cancer agent. The aptamer and anti-cancer agent may be associated with one another via any suitable means. The aptamer and anti-cancer agent may be associated with one another directly, or indirectly. In this context, by "indirectly associated" is meant that the aptamer is associated with a carrier, and the anti-cancer agent associated with the carrier, rather than directly to the aptamer itself.

Merely by way of example, in one suitable embodiment the aptamer and anti-cancer agent may be conjugated with one another. In a suitable embodiment the anti-cancer agent may be encapsulated by, or attached to (for example covalently or non-covalently) a suitable carrier. In such embodiments an example of a suitable carrier may be selected from the group consisting of: a nanoparticle (such as a nanoshell); and a dendrimer. Suitably, nanoparticles may encapsulate, or be coated by, an anti-cancer agent. Dendrimers may also encapsulate anti-cancer agents, or anti-cancer agents may be attached to peripheral groups of the dendrimer.

The anti-cancer agent may be any such agent known to those skilled in the art that it is desired to target to a site of cancer cells, such as a tumour. Merely by way of non-limiting example, in a suitable embodiment the anti-cancer agent may be selected from the group consisting of: a radionuclide; a nanoparticle, such as a nanoshell; a nanocage; a gene silencing agent; and a cytotoxic compound. In suitable embodiments aptamers of the invention may be associated with any of, or any combination of, these anti-cancer agents.

Radionuclides and cytotoxic compounds may have an inherent ability to kill cancer cells to which they are targeted, while nanoparticles (such as nanoshells) or nanocages are able to absorb energy when illuminated so that their temperature increases, allowing them to kill cancer cells to which they are targeted—a technique that is sometimes referred to as photodynamic therapy. Photodynamic therapy may also make use of near infrared dyes which, when illuminated, degrade to release reactive oxygen species able to kill nearby cells. It will be appreciated that dyes of this sort also constitute anti-cancer agents that may be associated with aptamers in accordance with the present invention.

Gene silencing agents are able to prevent or inhibit the process of gene expression, by interfering with either transcription or translation. Depending on the nature of the gene to be silenced, gene silencing agents may have inherent anti-cancer activity, or may be suitable for use as an adjunct to other anti-cancer therapies.

Suitable examples of gene silencing agents may be selected from the group consisting of: siRNA molecules; ribozymes; and antisense oligonucleotides. The gene to be silenced may be selected with reference to known properties of the cells to which the selected aptamer of the invention (associated with the gene silencing agent) binds. For example, the gene to be silenced may be a gene encoding the ligand to which the aptamer binds.

As discussed elsewhere in the present disclosure, the inventors have identified that aptamers of the invention consisting of SEQ ID NO: 2 (also designated SA43 or GL43), SEQ ID NO: 2, or SEQ ID NO: 3 bind to a ligand (Ku70 or Ku80) in the Ku heterodimer. Without wishing to be bound by any hypothesis, the inventors believe that the ligand bound by these aptamers is most likely Ku70.

The skilled person will appreciate that the biological function of the Ku heterodimer lies in DNA repair, and that as a consequence this aptamer will be particularly well suited to the targeting of cancer cells that have been exposed to irradiation or to DNA-damaging agents.

Furthermore, recognition that aptamers of the invention are able to bind ligands within the Ku heterodimer may make such aptamers of notable use for the targeting of gene silencing agents. Merely by way of example, when aptamers of the invention comprising SEQ ID NO: 1, 2, or 3 (or ligand binding fragment thereof) are associated with gene silencing agents directed to Ku70 and/or Ku80, such aptamers may be used in combination with other anti-cancer therapies in which radioactive or other DNA-damaging approaches are used to kill cancer cells. The ability aptamers of the invention to effectively target cancer cells expressing the Ku heterodimer, and then to prevent or inhibit the expression (and thus function of this heterodimer) will reduce DNA repair, and thus increase the effectiveness of the DNA-damage-based therapy.

Accordingly, it may be desired to that aptamers comprising SEQ ID NO: 1, 2, or 3, or ligand-binding fragments of such aptamers, comprise a gene silencing agent that prevents or inhibits gene expression of Ku70 and/or Ku80. Suitable gene silencing agents (such as siRNA molecules) may be selected or designed by the skilled person with reference to the known sequence of the genes, and mRNA, encoding Ku70 and/or Ku80. Aptamers in accordance with these embodiments are suitable for use in as adjuncts to cancer therapy using DNA-damaging agents (e.g. chemotherapeutic agents or radiation).

Indeed, the advantages provided by these combinations of aptamers of the invention and gene silencing agents are such that, a further aspect of the invention provides an aptamer comprising SEQ ID NO: 1, 2, or 3, or a ligand binding fragment of such an aptamer, associated with a gene silencing agent that prevents or inhibits gene expression of Ku70 and/or Ku80. The gene silencing agent may be selected from the group consisting of: siRNA molecules; ribozymes; and antisense oligonucleotides.

In a further aspect the invention provides a pharmaceutical composition comprising an aptamer of the invention, or a ligand-binding fragment thereof, and a pharmaceutically acceptable excipient. The aptamer of the invention may optionally be associated with an anti-cancer agent, in the manner considered above. In a suitable example the pharmaceutical composition may be in the form of an injectable composition. Alternatively, the pharmaceutical composition may be formulated for oral administration.

The present invention also provides an aptamer according to the invention, or pharmaceutical composition of the sort considered above for use in the prevention and/or treatment of cancer. As discussed elsewhere herein, the cancer to be prevented and/or treated may be brain cancer. The pharmaceutical composition may be formulated to provide a therapeutically effective amount of the aptamer in a dosage unit of the pharmaceutical composition. Alternatively, or additionally, the pharmaceutical composition may be formulated to provide a therapeutically effective amount of an anti-cancer agent associated with the aptamer.

In a further aspect the present invention provides a method of preventing and/or treating cancer in a subject, the method comprising administering to a subject in need thereof a therapeutically effective amount of a pharmaceutical composition of the invention.

As referred to above, the aptamers of the present invention, and ligand-binding fragments thereof, are suitable for use in diagnostic applications. In such applications, the aptamer, or ligand-binding fragment, may be associated with a detection moiety. A detection moiety in the context of these embodiments of the invention may be any compound or group that may be associated with the aptamer, and detection of which provides an indication of the location of the aptamer. Thus detection of an immobilised detection moiety associated with an aptamer of the invention may indicate that the aptamer of the invention has bound to cancer-associated ligands, for example in a patient or in a sample from a patient.

Merely by way of example, a suitable detection moiety may be selected from the group consisting of: a radionuclide; a dye; a fluorophore; a nanoparticle (such as a nanoshell); a nanocage; and a chromogenic agent (for example an enzyme, such as horseradish peroxidase, that is capable of bringing about a chromogenic change in a chromogenic substrate).

The properties of nanoparticles, such as nanoshells, or nanocages that make these suitable for use as anti-cancer agents (the ability to absorb radiation in a region, such as near infrared, of the spectrum at which biological tissues absorb very little) also make these agents suitable for use as detection moieties.

The aptamers of the invention, optionally associated with detection moieties, for example in the manners considered above, may be used it the diagnosis or clinical grading of cancer. In an aspect of the invention there is provided a method of diagnosing or grading cancer in a subject suffering therefrom, the method comprising providing to the patient an amount of an aptamer of the invention in combination with a detection moiety, and determining the retention of the detection moiety, and thus the aptamer, in the subject. Retention of the aptamer of the invention (and the associated detection moiety) may indicate the presence of cancer in the subject. Additionally, the retention of the aptamer (and associated detection moiety) in the subject may indicate the clinical grade of the cancer from which the subject is suffering.

Another application of the aptamers of the invention lies in their potential use as research reagents. There are a range of circumstances in which it may be desirable to have agents available that are able to bind specifically to ligands associated with cancer cells. Merely by way of example, these may include cell culture or cell separation assays. The aptamers of the invention, or their ligand-binding fragments, suitable for use in this manner may comprise a detection moiety, which may be of the sorts discussed above. For example, in cases where it is desired to use the aptamers of the invention in research reagents facilitating flow cytometric sorting of cells, the aptamers may be associated with a fluorophore, as considered previously. Alternatively, aptamers of the invention for use as research reagents may be associated with other functional moieties. Merely by way of example, the aptamers may be associated with magnetic beads that allow alternative strategies by which cells expressing ligands bound by the aptamers of the invention may be separated.

While the aptamers of the invention may be able to bind to ligands associated with a wide range of cancer, and hence may have applications in, for example the therapy, diagnosis, or grading of any such cancer, in a preferred embodiment the cancer in question may be brain cancer. Suitable examples of brain cancers that may benefit from therapeutic or diagnostic applications of the aptamers of the invention include, but are not limited to those selected from the group consisting of: gliomas; meningiomas; pituitary adenomas; and nerve sheath tumours. Of these examples, the aptamers of the invention may be particularly useful in therapeutic or diagnostic applications relating to gliomas.

In a further embodiment, the invention provides a kit comprising an aptamer of the invention, or a ligand-binding fragment thereof. A kit of the invention may comprise one, more than one, or all of the aptamers of the invention herein disclosed. The kit of the invention may optionally comprise further components, such as detection moieties that may be used for localisation of bound aptamers. The kit of the invention may comprise diluents or chromogenic substrates conventional in histochemistry products. The kits of the invention may comprise information regarding the practice of a diagnostic test using the aptamer(s) of the invention.

The invention will now be further described with reference to the following Experimental Results, and accompanying Figures, in which:

FIG. 1 sets out representative photomicrographs illustrating the results of confocal imaging, with Cy3 labelled aptamers and DAPI nuclear counterstain, in a range of cell types.

FIG. 2 sets out representative plots achieved in a flow cytometry study using Cy3 labelled aptamers with a range of cell types.

FIG. 3 illustrates active uptake of aptamers of the invention by glioma cells.

FIG. 4 summarises the data shown in FIG. 3.

FIG. 5 sets out representative photomicrographs showing the results of labelling in non-cancerous brain or samples from Grade I-IV gliomas with aptamers of the invention or with a negative control aptamer.

Figure 13:
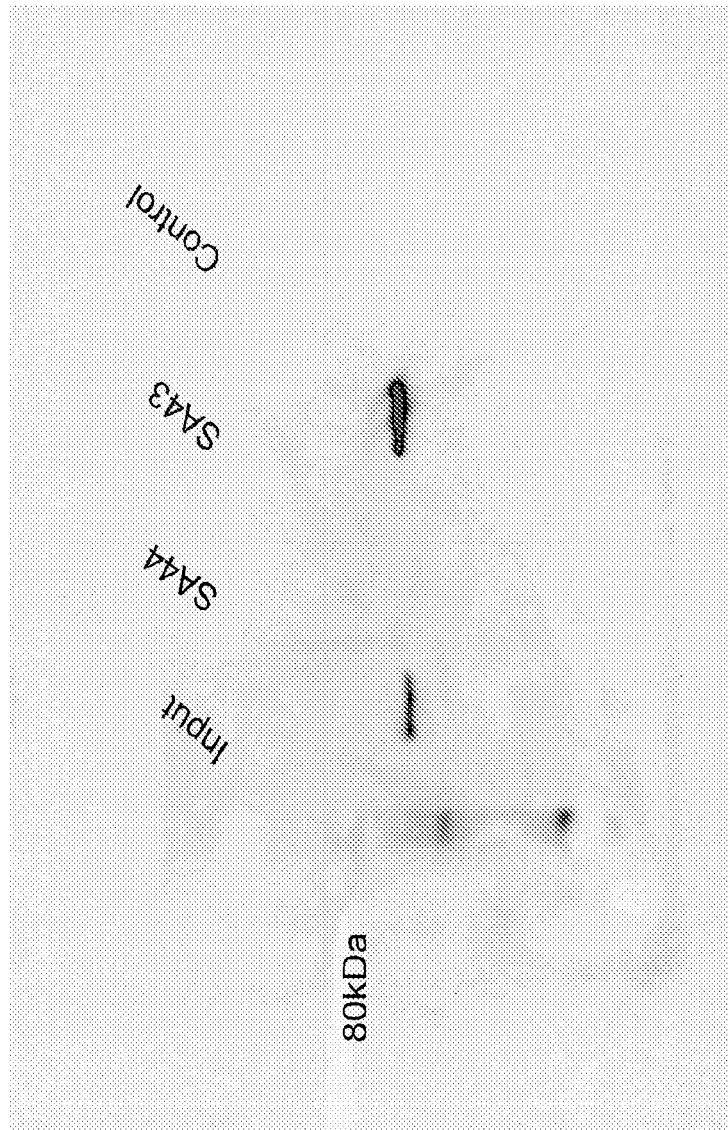

FIG. 13 illustrates the results of Western blotting on lysates of U87 cells. This figure illustrates the ability of the aptamers of the invention SA43 to aptamerprecipitate and thus "pull down" Ku 70 from cell lysates, thus demonstrating the specificity of SA43 for the Ku complex. The lane labelled "input" is a whole cell lysate. Lanes labelled "SA43", "SA44", and "Control" respectively illustrate the products bound within U87 cell lysates by the aptamers of the invention SA43, the control aptamers "SA44", and a whole cell lysate without aptamer. Proteins from the gel were transferred to a nitrocellulose membrane, and the membrane probed with an antibody specific to Ku 70. As can be seen, only the "Input" and "SA43" lanes contained Ku protein, indicating the specificity of SA43.

EXPERIMENTAL RESULTS 1

Binding of the aptamers of the invention to ligands associated with cancer cells, and the specificity of this binding was investigated and demonstrated in the following studies.

Aptamers of the invention (as set out below) were used to label cultured cancer and non-cancer cells and to perform flow cytometry on such cells, and also to label histological sections of non-cancerous brain tissue, and also sections of tissue taken from gliomas of Grades I to IV.

The aptamers used were as follows:
SEQ ID NO: 1 (also referred to as SA44 or GL44)
SEQ ID NO: 2 (also referred to as SA43 or GL43)
SEQ ID NO: 3 (also referred to as SA56 or GL56)

As a control, the same labelling protocols were also followed using SEQ ID NO:4 (also referred to as CL44) or a randomly generated sequence (designated "neg aptamer") as follows:

CCG UUA AUU AGG CCC UUA AAU GGC AUA AAA UUU GAA AGG GAA U

More details of the studies undertaken are provided below.

Materials and Methods
Cell Lines and Cell Culture:

The experiments were carried out using different grades of human glioma cell lines including 1321N1 (grade II astrocytoma), U87MG (grade IV glioblastoma), T98G (grade IV glioblastoma) and non-cancerous foetal astrocytes SVGp12 (Table 2.1). The cell lines were obtained from the European Collection of Cell Cultures (ECACC), UK and American Type Culture Collection (ATCC). Two other non-glioma cell lines were also utilised including MCF-7 (breast cancer) and T24 (bladder cancer). Media and supplements for each cell line used were in accordance with recommendation of ECACC and ATCC. All cell lines were maintained in a 37° C. humidified incubator with 5% $CO_2$ and 75 $cm^2$ tissue culture flasks (Thermo Scientific Nunc, UK). The cell lines were harvested when they reached 70-80% confluence and were used between passages 5-25.

Cellular Uptake and Localisation:
Confocal Microscopy:

Glial cell lines (1321N1, U87MG, T98G and SVGp12), breast cancer cell line (MCF-7) and bladder cancer cell line (T24) were cultured and seeded on coverslips of 24 well plates at a seeding density of $1 \times 10^4$ cells/ml in their individual media supplemented with FBS and penicillin/streptomycin mixture. Confluent cell lines were then incubated with a particular concentration aptamer at 37° C. for 90 minutes. The cells were then washed 3× with PBS to remove the unbound aptamer. The cells were then fixed with 4% Paraformaldehyde (PFA) for 15 minutes at room temperature. After fixing, the cells were counter-stained with VECTASHIELD mounting medium with DAPI (Vector laboratories, UK) to stain the nucleus. Images of aptamer binding to cells were acquired using a Zeiss LSM 510 META confocal microscope applying the same instrument settings (Amplifier gain: 1, Detector gain: 1092, Amplifier offset: −0.06).

Flow Cytometric Assay:

Glial cell lines (1321N1, U87MG, T98G and SVGp12), breast cancer cell line (MCF-7) and bladder cancer cell line (T24) were allowed to grow on 24 well plates until they reached 80% confluency. The cells were washed with 1×PBS and incubated with suitable concentration of the aptamers at 37° C. (5% $CO_2$) for 90 minutes. The cells were subsequently washed 3 times with 1×PBS followed by the treatment of 1× trypsin into each well and incubated at 37° C. for 2 minutes to detach the adherent cells. 2 minutes after the trypsin treatment, the well plates was tapped gently and viewed under the inverted light microscope to ensure for the detachment of cells. A volume of 0.3 ml of media was then added and the cell suspension was then transferred to an eppendorf tube. The cells were then centrifuged at 224 g for 5 minutes. After centrifugation, the supernatant was aspirated and the pellet was then flicked and resuspended with 300 µl of 1×PBS and mixed well and ready for flow cytometry analysis. Analysis was performed on flow cytometer using PE (phycoerythrin) laser at an excitation at 488 nm and emission at 578 nm where 10,000 events were collected for each sample.

Immunohistochemistry Using Biotin Labelled Aptamers:

The study also involved screening of the aptamers on a serial tissue sections from BTNW bank with different grades of glioma including grade I, grade II, grade III, grade IV glioblastoma and non-cancerous brain from 45 different patients.

For aptamer staining, each excised tumour tissue sample and non-tumour portion were fixed and serially sectioned (4 mm), as formalin-fixed, paraffin-embedded slides by pathologists from the hospital. These paraffin-embedded tissue slides were deparaffinised with 2 changes of Histoclear, 15 minutes each and rehydrated through graded ethanol, 5 minutes each. The tissue slides were rinsed with distilled water and then underwent antigen retrieval step with 0.01 M citrate buffer at 97° C. for 20 minutes before the experiment. The sections were rinsed in PBS twice for 2 minutes each. To mask endogenous biotin binding, sections were treated with biotin-blocking solution (Vector laboratories) for 30 minutes and then washed 3 times with PBS, following manufacturer's instructions. The tissue slides where then incubated with 100 nM biotin labelled aptamers for 60 minutes at room temperature. The slides were then washed 3 times with PBS, 5 minutes each wash. The slides were then incubated with VECTASTAIN® ABC reagent for 30 minutes at room temperature. After three washes with PBS solution, the tissues sections were subsequently treated with 200 µl of DAB peroxidase substrate solution (Dako) for colour development at room temperature for 10 min. Counterstaining of the cell nuclei in tissue sections was performed with the haematoxylin solution for 5 minutes following routine laboratory protocol to dehydrate and mount the sections. The treated tissues were then examined under a light microscope.

Screening of Cy3 Labelled Aptamers on Cell Lines

Aptamers SA44 (GL44), SA43 (GL43), SA56 (GL56), control aptamer CL44, and "neg" were tagged with Cy3 fluorescent dye. Binding of the tagged aptamers was screened on cell lines and their binding specificity was analysed using Z stacks and 3D confocal imaging. Representative photomicrographs illustrating the results of the confocal imaging are set out in FIG. 1.

Figure 1:
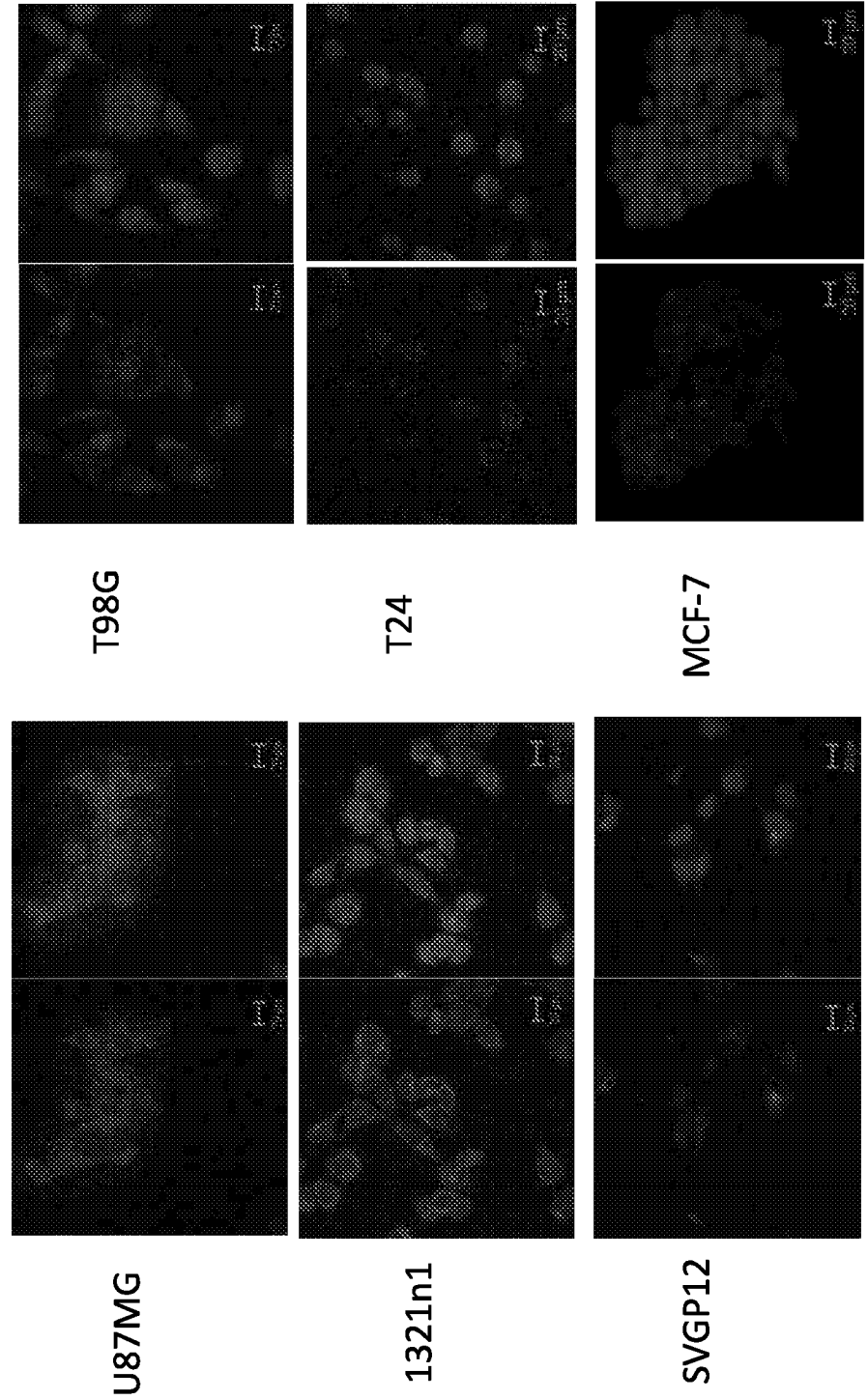
Figure 1:
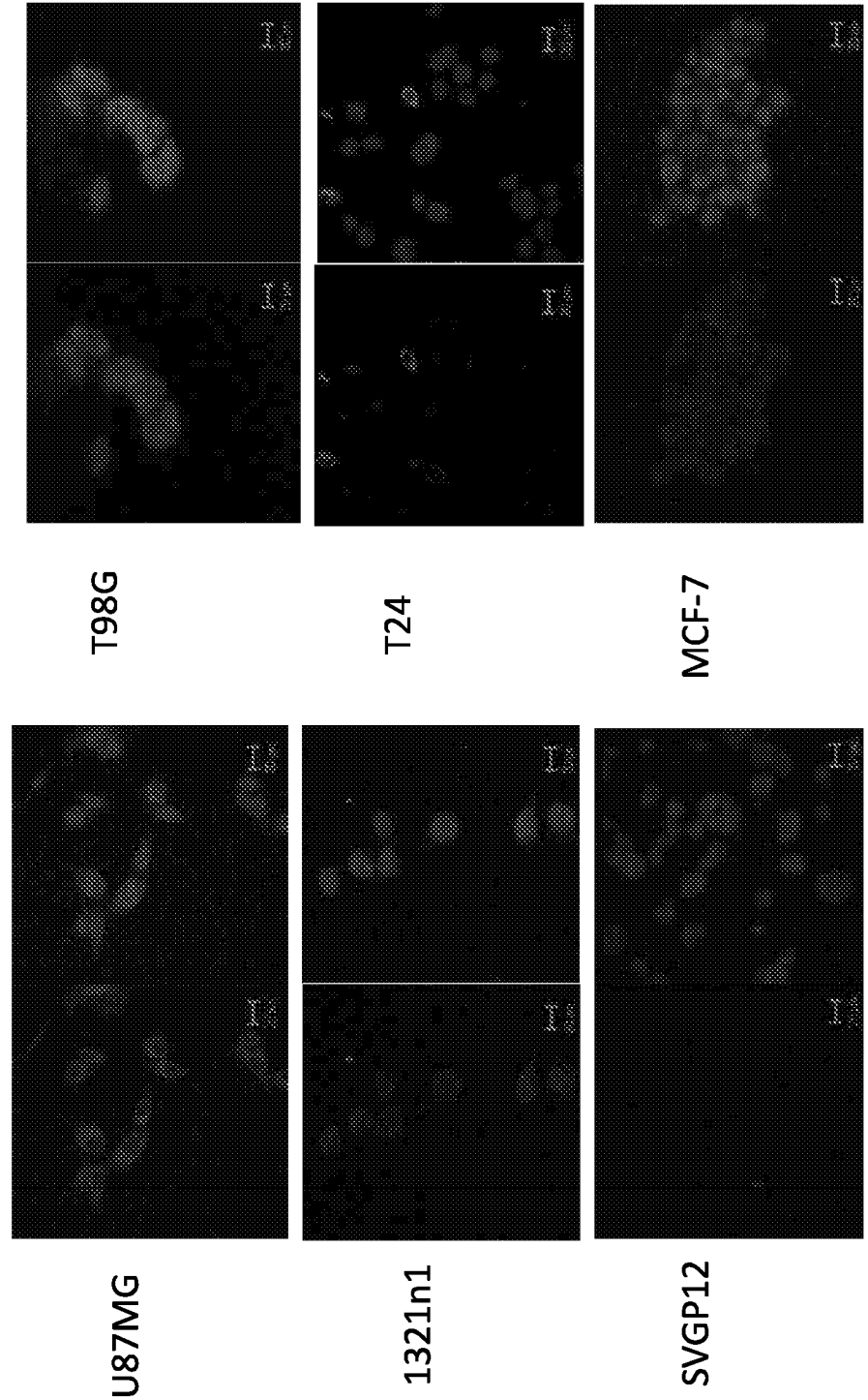
Figure 1:
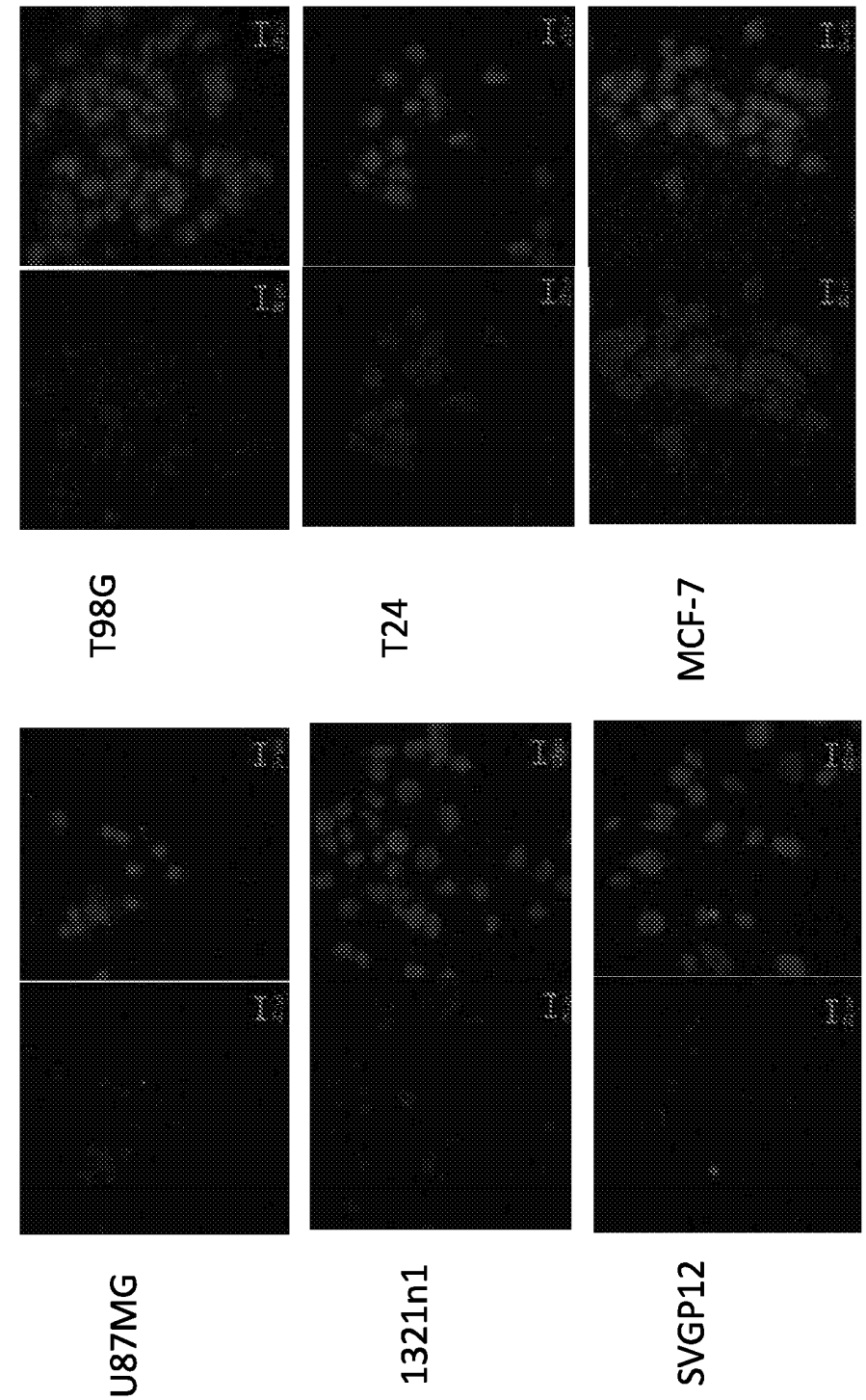
Figure 1:
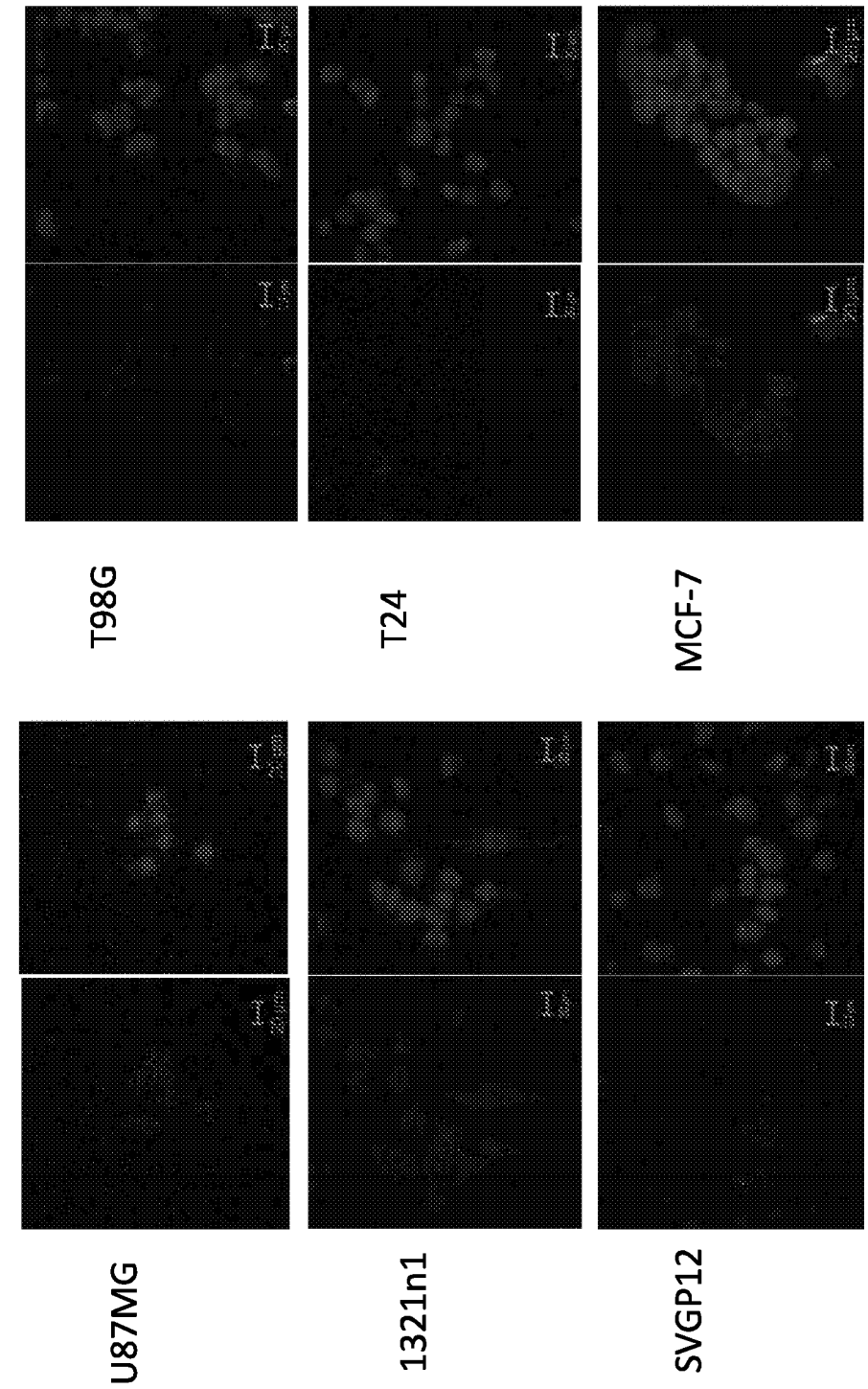

Binding of aptamers was investigated in connection with the following cell lines:

U87MG—cells derived from a Grade IV glioma
1321n1—cells derived from a Grade II glioma
SVGp12—non-cancerous foetal astrocyte cells
T98G—cells from a Grade IV glioma, though less tumourigenic than U87MG
T24—cells of a bladder cancer cell line
MCF7—cells of a breast cancer cell line Aptamers SA44 (GL44) and SA43 (GL43) showed higher binding capacity on U87MG glioma cell line compared to non-cancerous SVGp12 cells. As can be seen in FIG. 1, the aptamers were selective for cancerous, rather than non-cancerous, cells.

Figure 2:
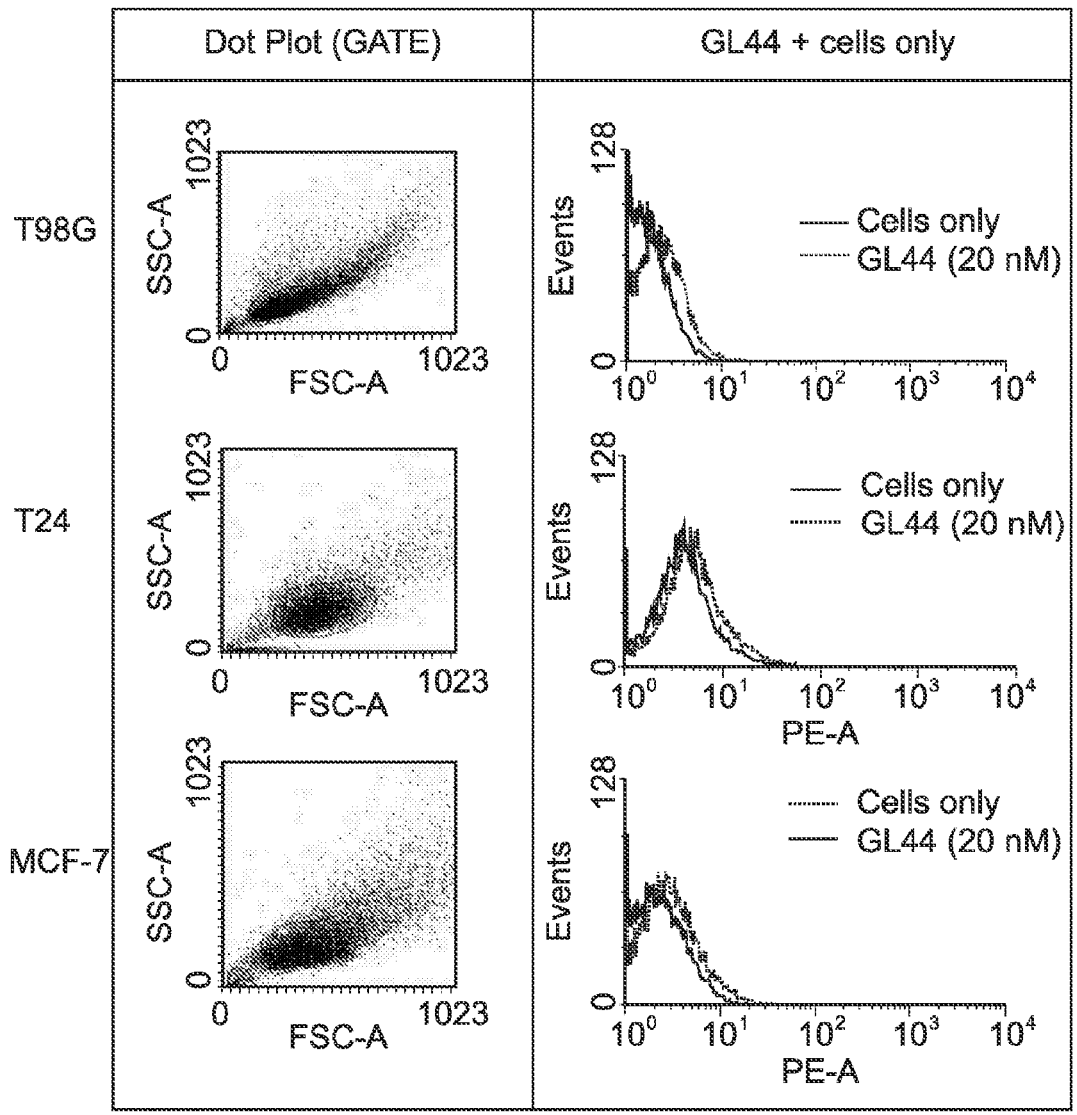
Figure 2:
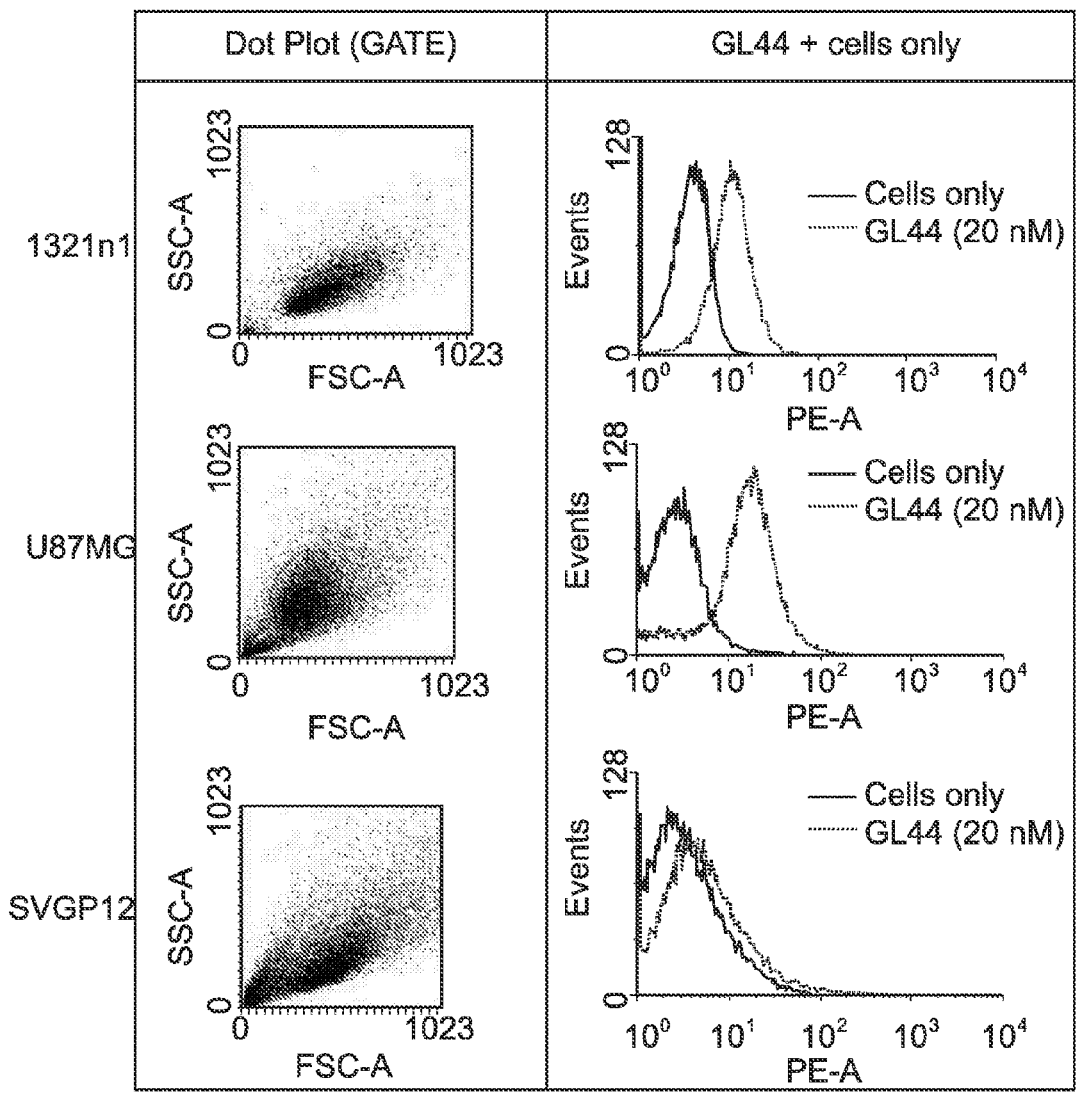
Figure 2:
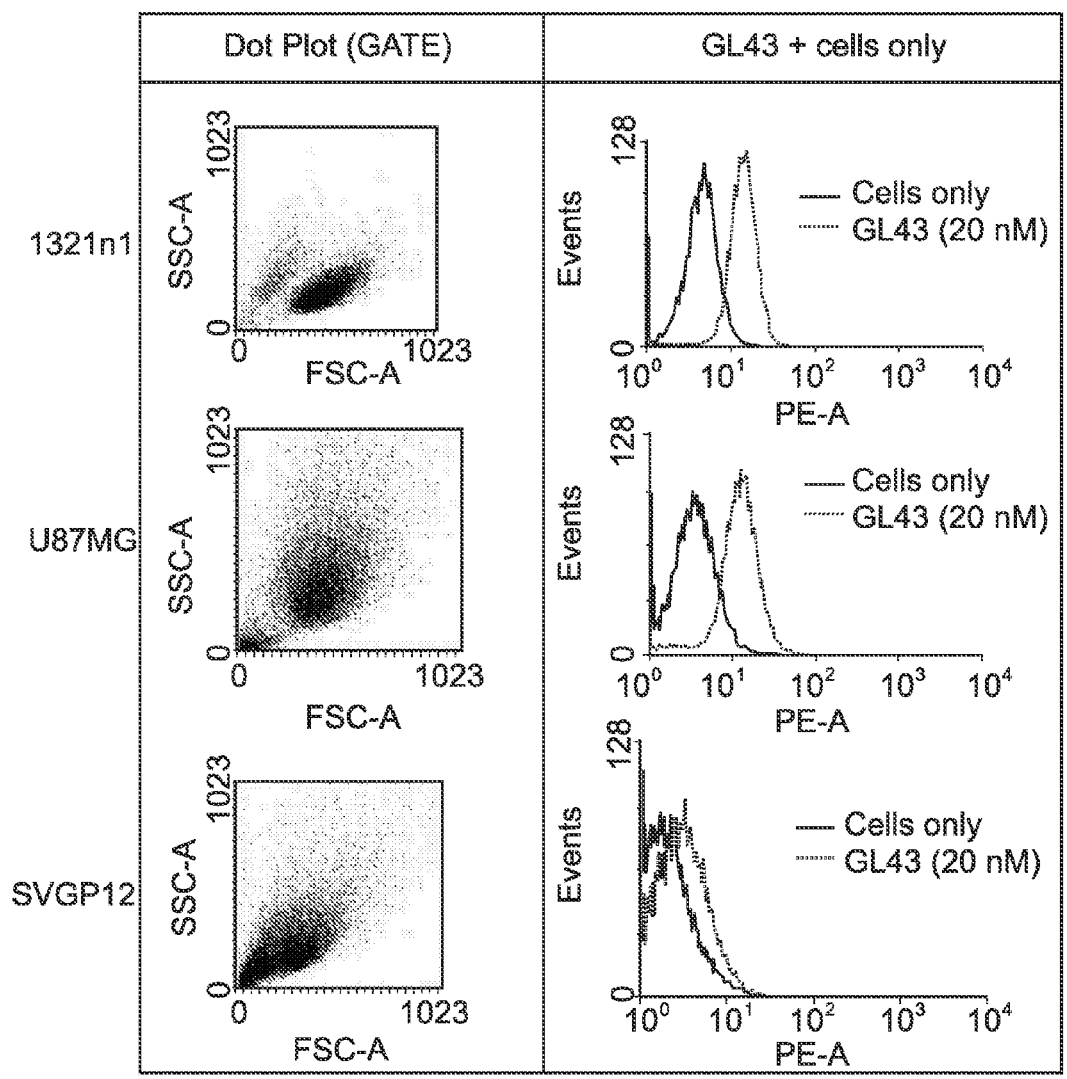
Figure 2:
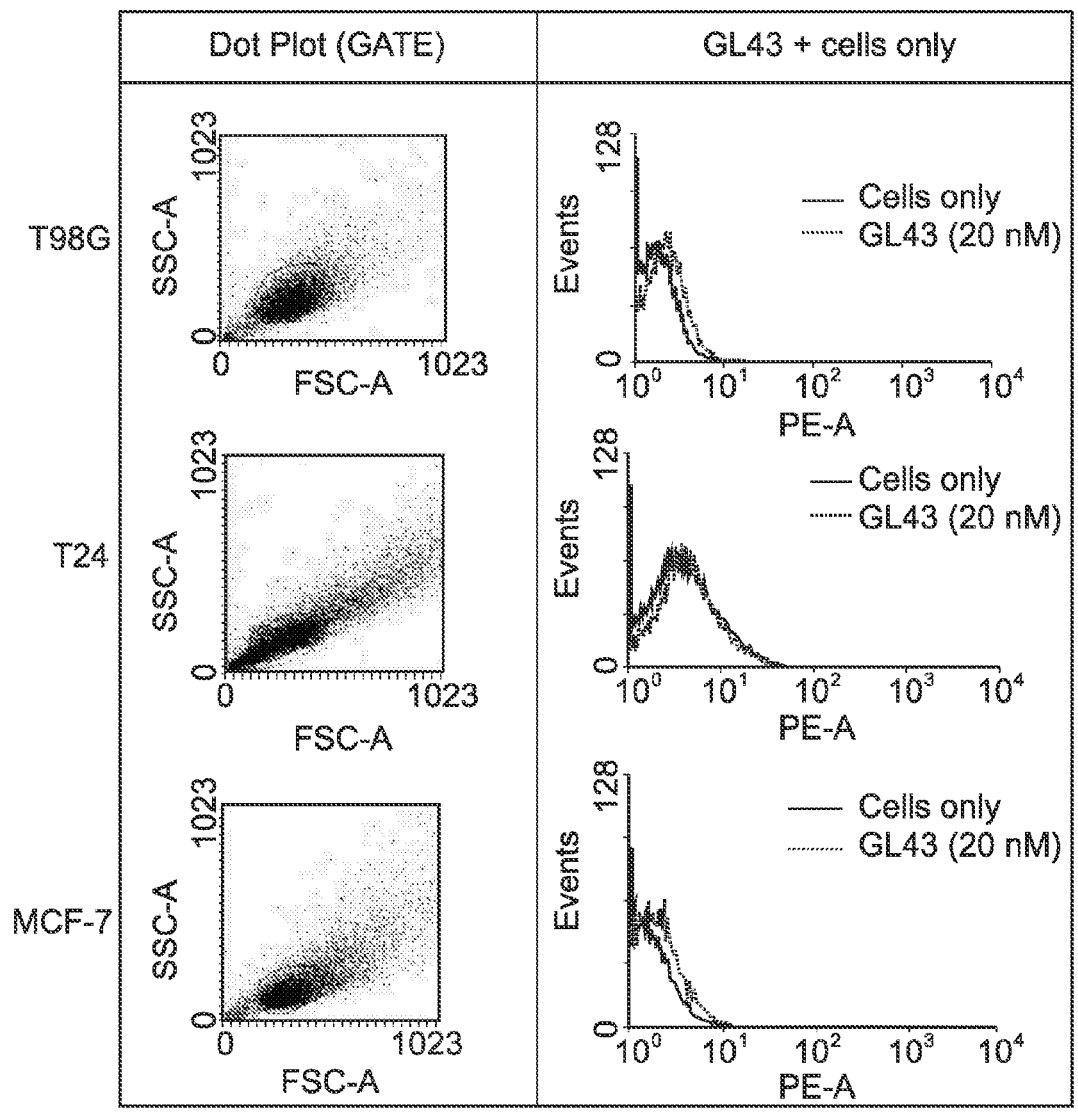
Figure 2:
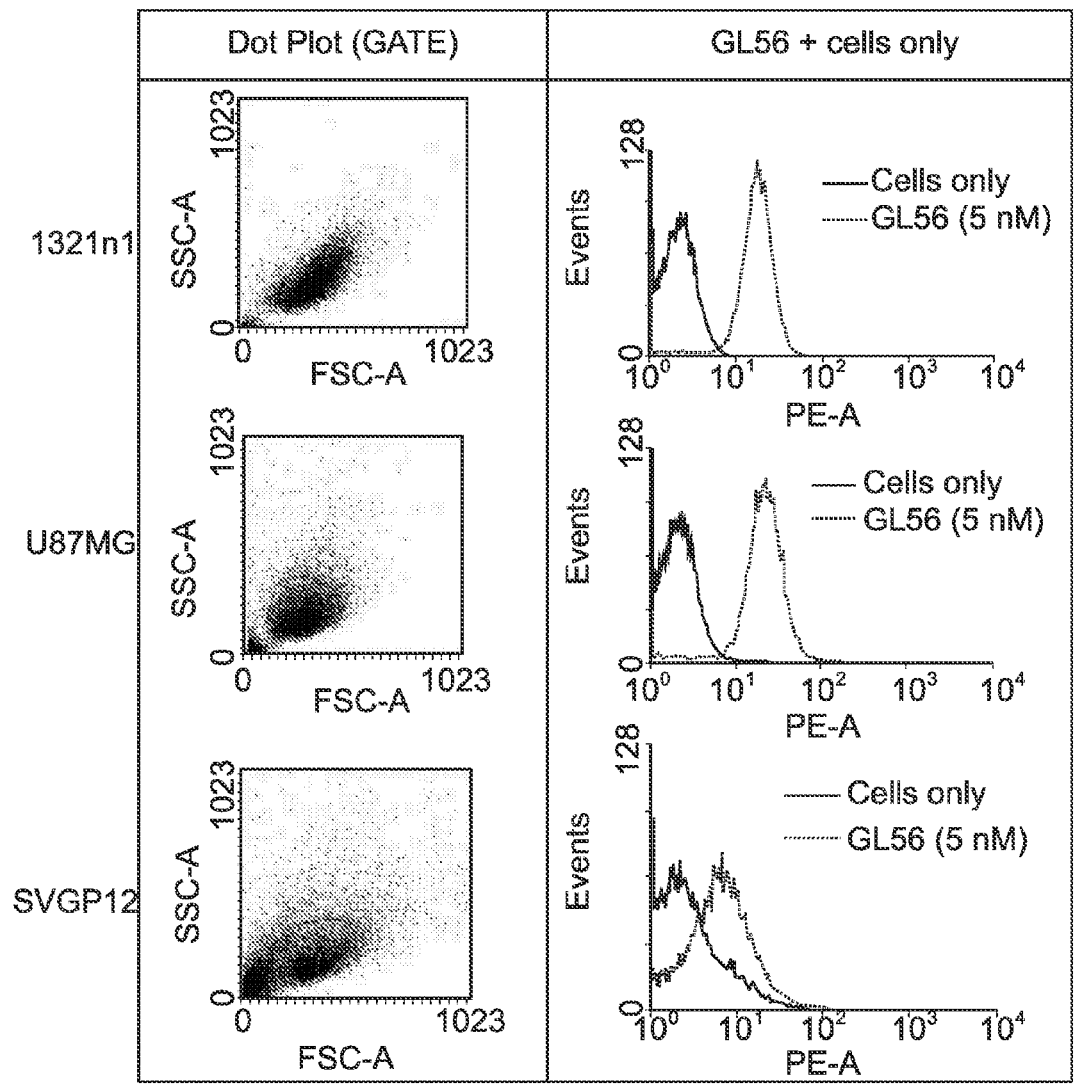
Figure 2:
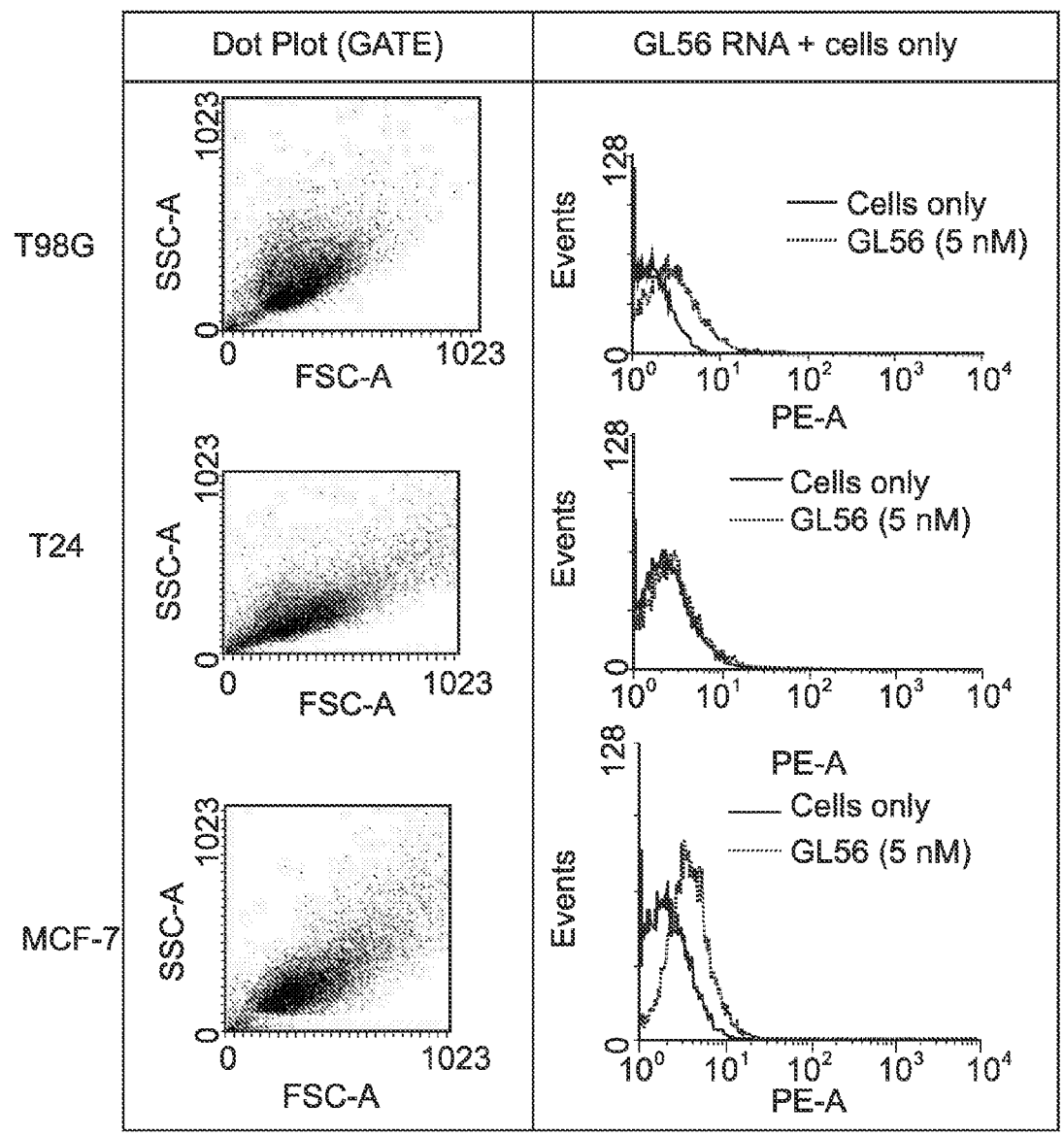
Figure 3:
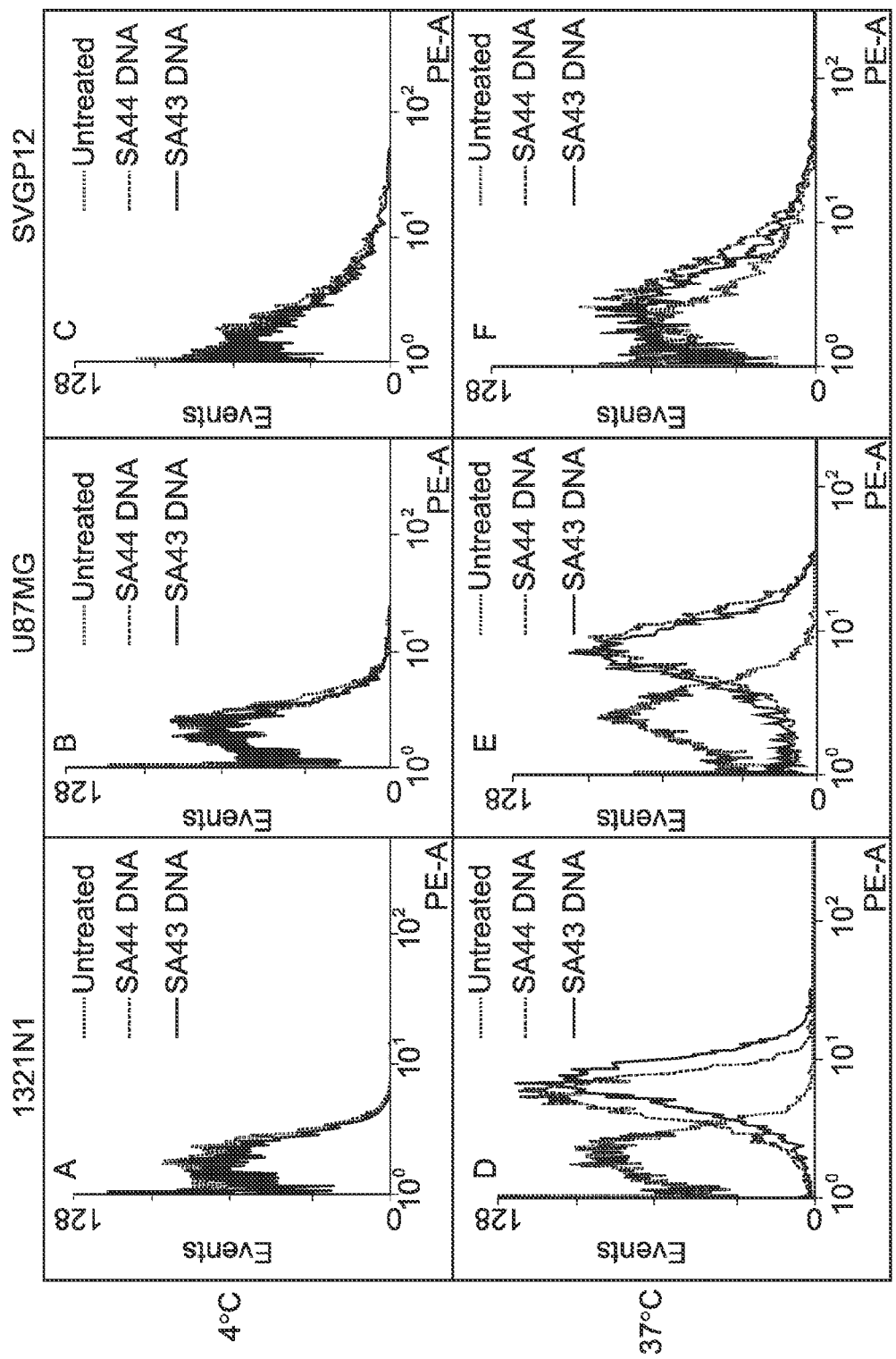

Binding of Cy3 tagged aptamers SA44 (GL44), SA43 (GL43) and SA56 (GL56) to the cell lines was also quantified using flow cytometry. Representative plots of the results achieved are shown in FIG. 2. The same pattern of aptamer binding, with specificity for U87MG as opposed to SVGp12 cells, was observed Active Uptake of the Aptamers of the Invention into Glioma Cells Results of the study investigating active uptake of the aptamers of the invention by glioma cells is shown in FIG. 3, and the results shown in this Figure summarised in FIG. 4.

Figure 4:
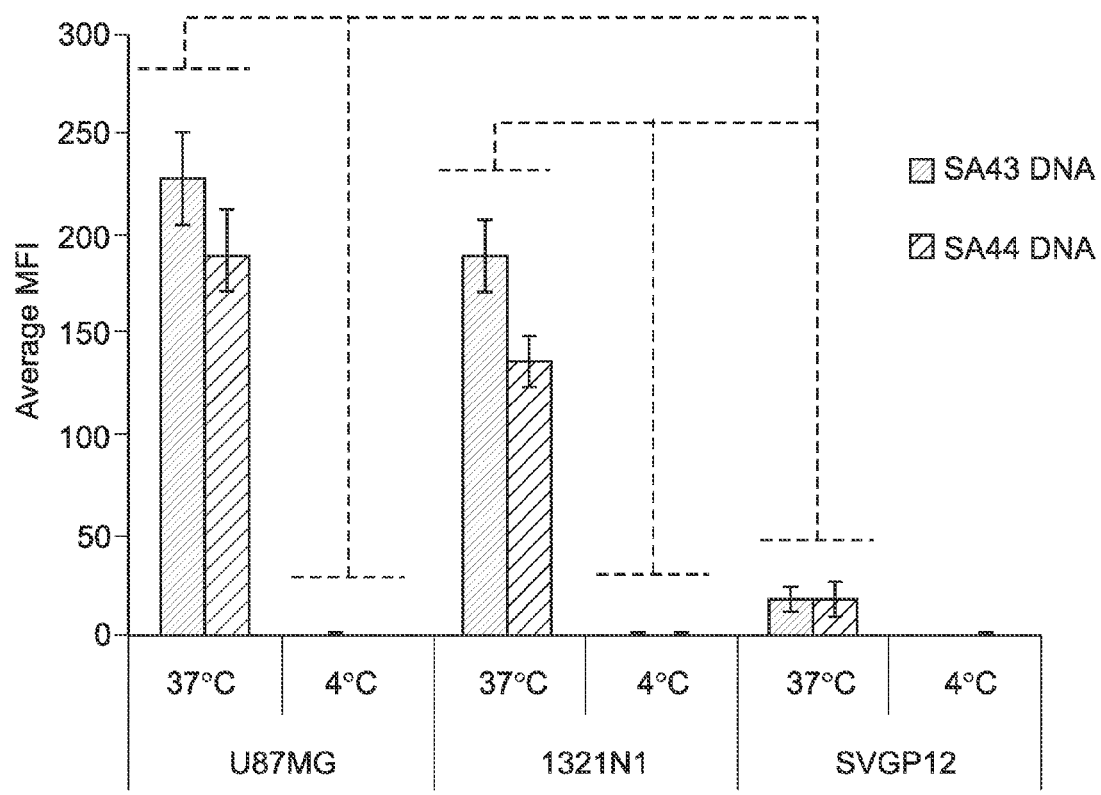

Briefly, FIG. 4 illustrates that when aptamers of the invention are incubated with cells of glioma cell lines at 4° C. there is substantially no uptake of the aptamers into cells. However, when the aptamers are incubated with examples of the same cell lines at 37° C., a temperature at which metabolic processes of the cells are active, the aptamers (here illustrated with reference to SA44 or SA43) are taken into the cells. This active uptake, results of which are summarised in FIG. 4, represents a useful process by which the aptamers of the invention are able to enter into glioma cells, consistent with the uses of these aptamers in therapeutic or diagnostic (such as labelling) applications.

Labelling of Tissues

Aptamers of the invention (as set out above), control aptamer CL44, or the "neg" negative control aptamer, were used to label histological sections of non-cancerous brain tissue, and also sections of tissue taken from gliomas of Grades I to IV.

In total the binding of each of these aptamers (the aptamers of the invention, control and the "neg" aptamer) was investigated in:

9 samples of non-cancerous brain,
7 samples of Grade I gliomas,
9 samples of Grade II gliomas,
10 samples of Grade III gliomas, and
10 samples of Grade IV gliomas.

Figure 5:
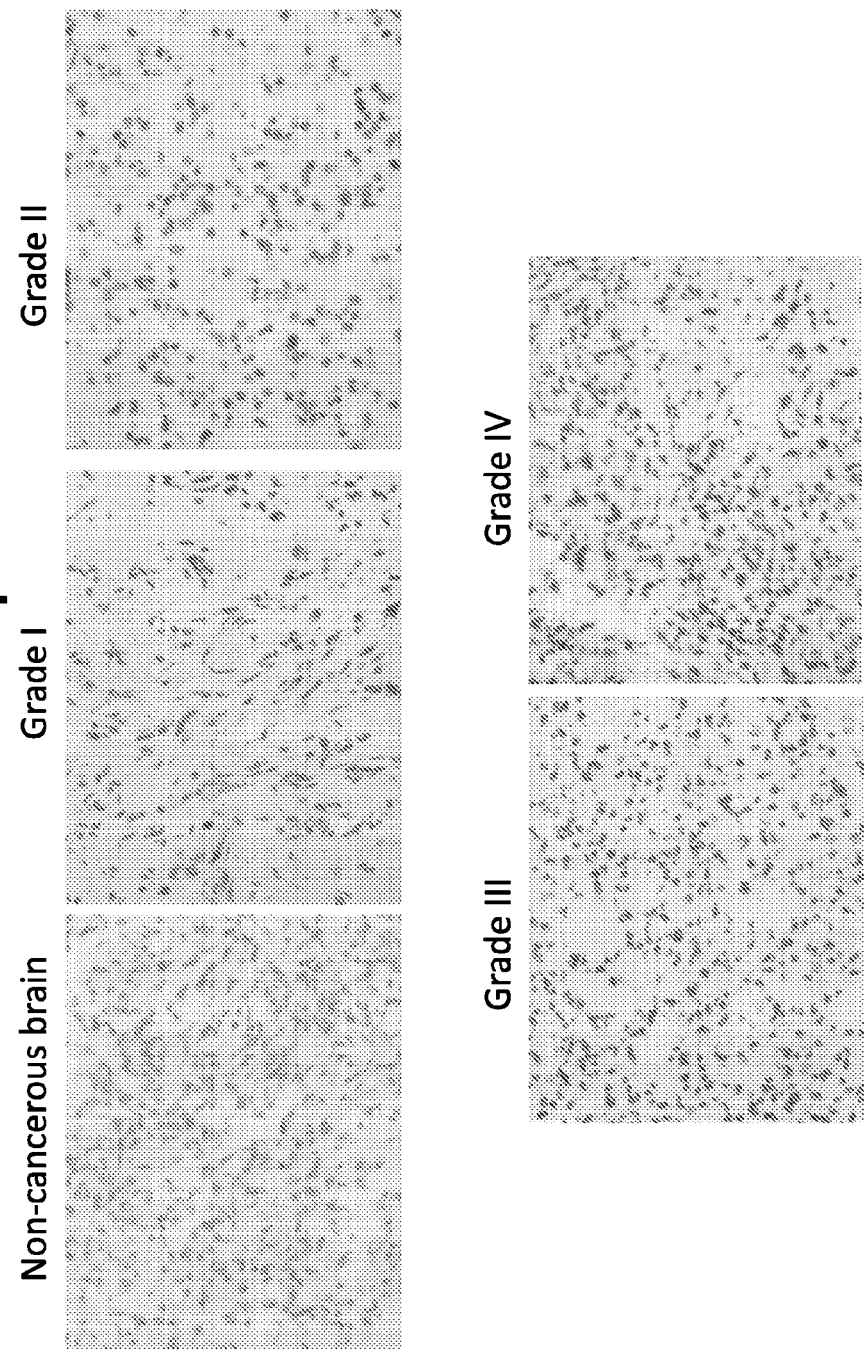
Figure 5:
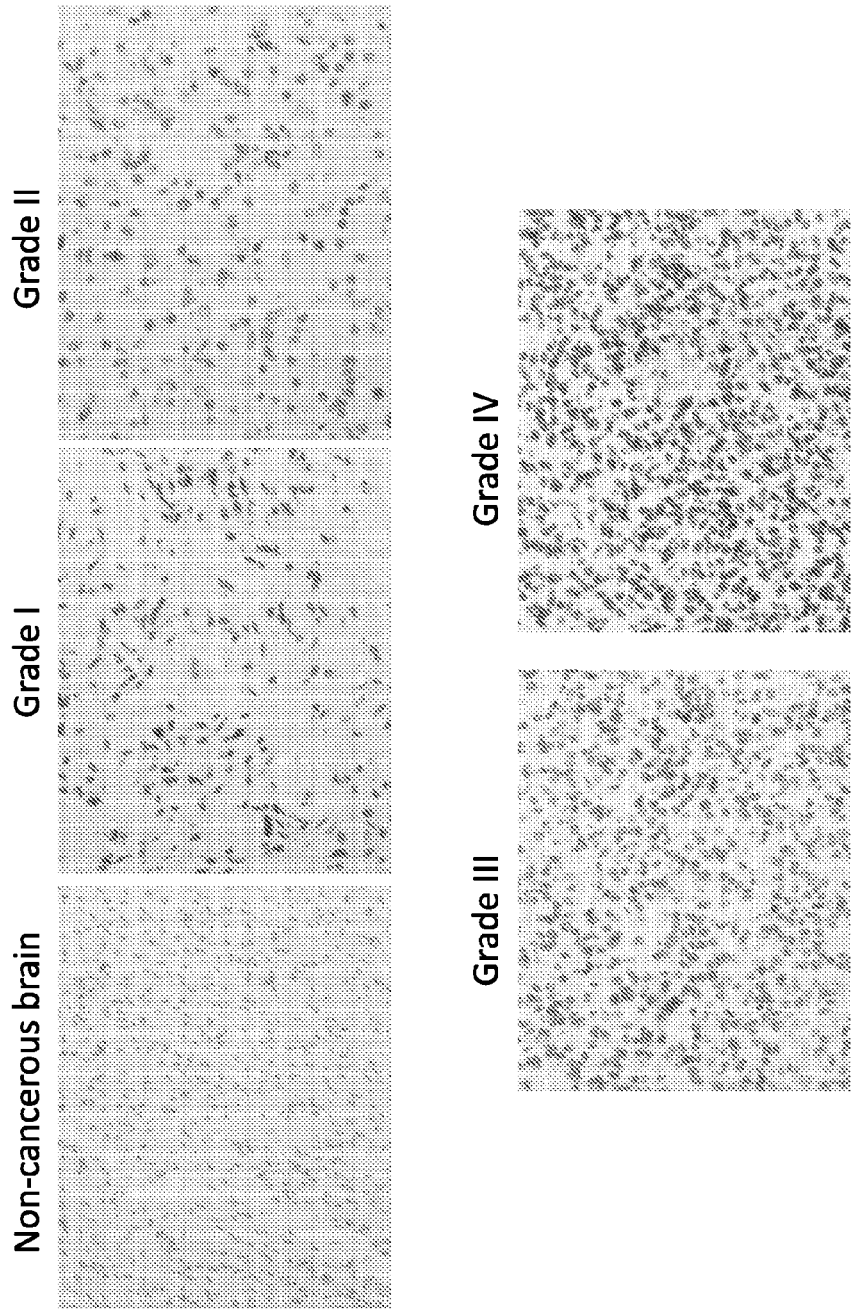
Figure 5:
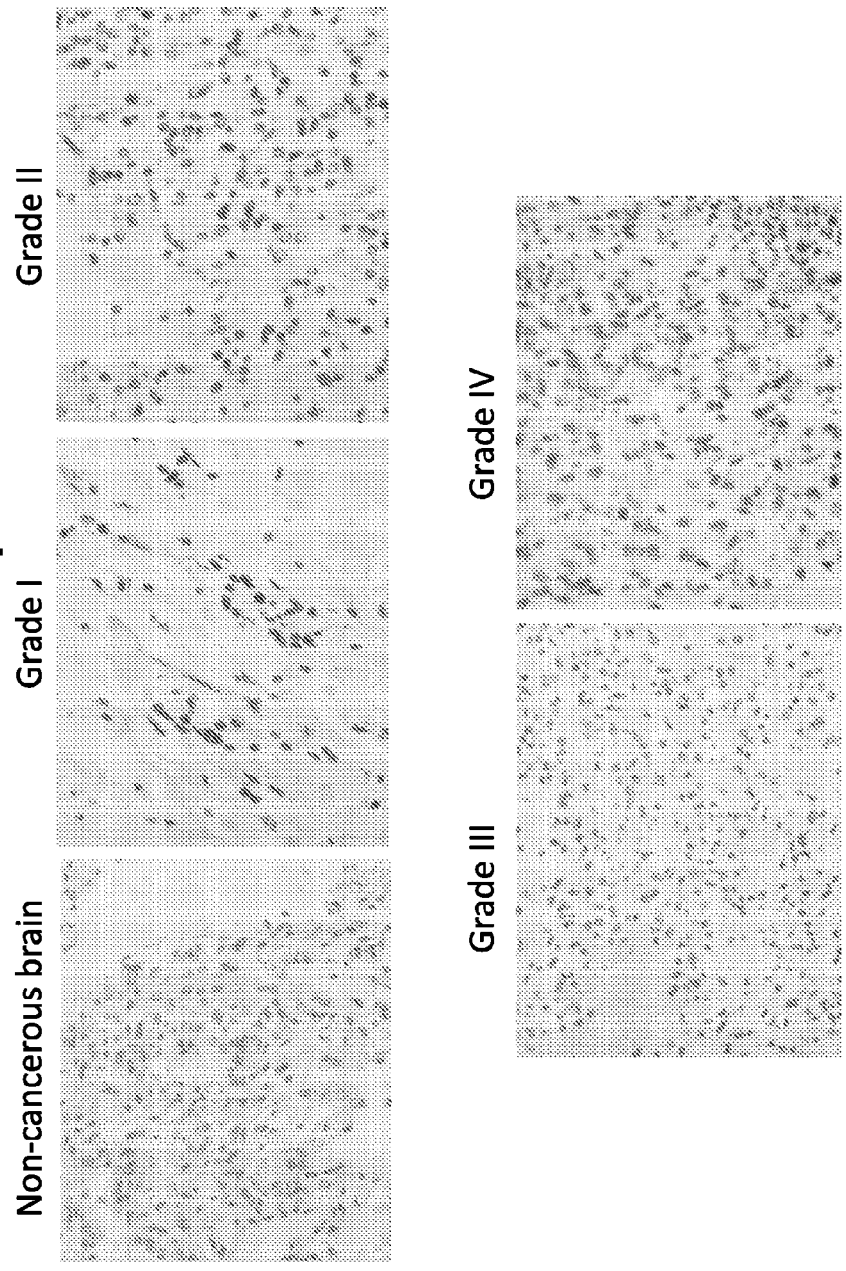
Figure 5:
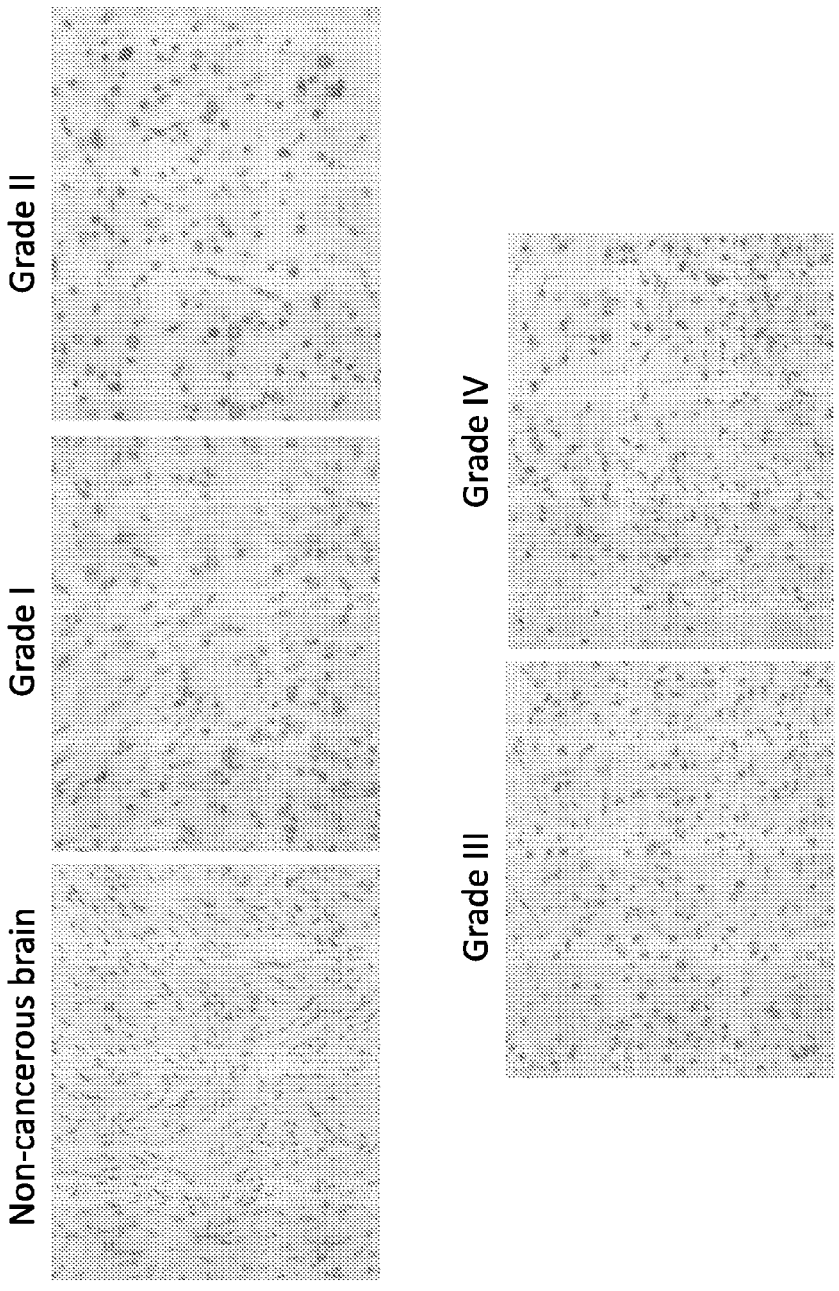
Figure 5:
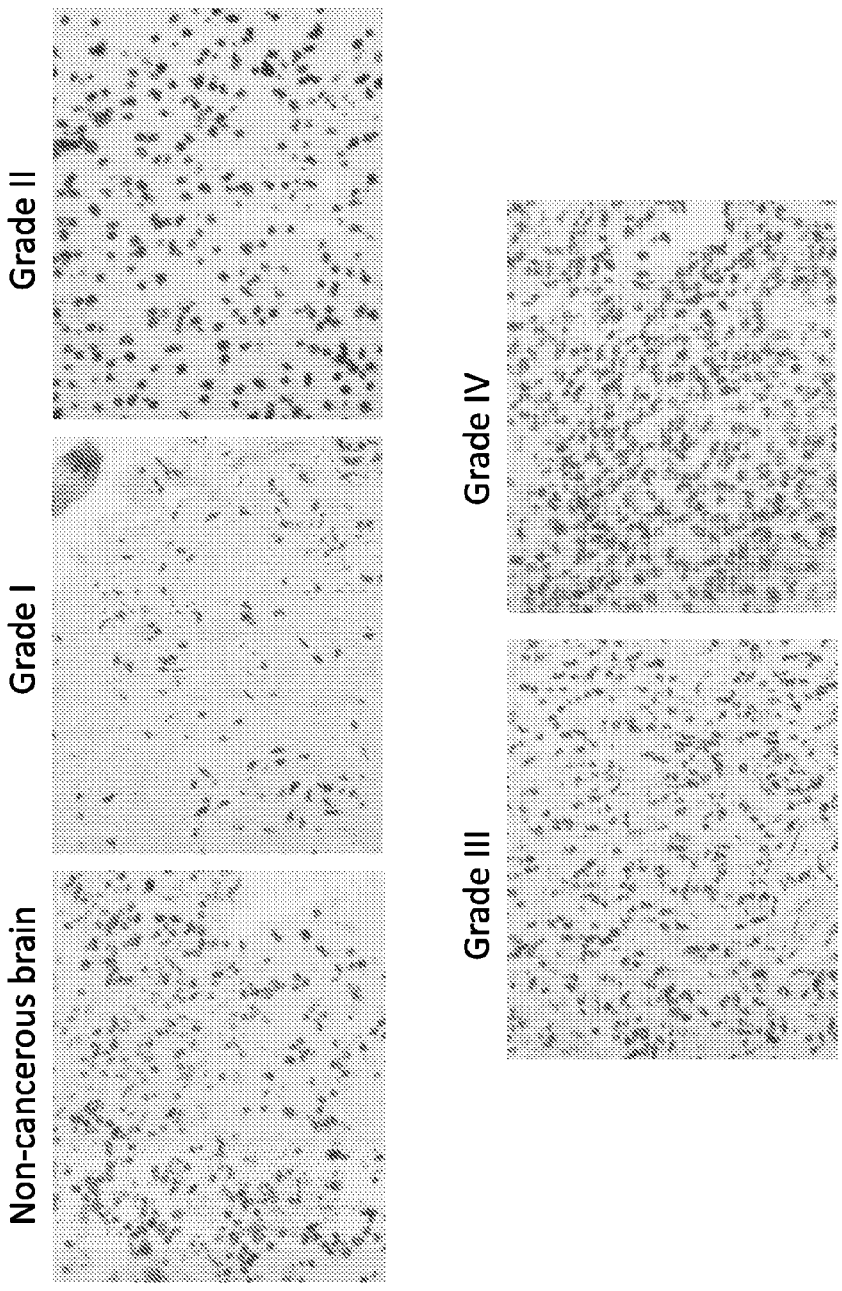

Representative photomicrographs showing the results of this labelling are set out in FIG. 5. Each panel of this Figure illustrates labelling of a different aptamer (either an aptamer of the invention, control or the neg aptamer) in non-cancerous brain or samples from Grade I-IV gliomas.

Specific binding of the aptamer is illustrated by the generation of a dark stain at the site of the labelling. Cell nuclei within the samples are visualised by haematoxylin counter-stain.

From reviewing the Figures, it can be seen that cellular labelling with the aptamers of the invention (but not the control or neg aptamer) was increased in gliomas as compared to non-cancerous tissue, and the extent of labelling rose as the Grade of glioma increased.

45 different primary tissues from grade I (n=7), grade II (n=9), grade III (n=10), grade IV (n=10) and non-cancerous brain (n=9) were screened with biotin labelled aptamers and quantified using an established IHC scoring system, details of which are shown in Table 1. A total score of ≤3 was considered as negligible binding.

TABLE 1

| Score for staining intensity | Score for proportion staining |
|---|---|
| 0 = no staining | 0 = no staining |
| 1 = weak staining | 1 = <1% staining |
| 2 = moderate staining | 2 = 1-10% staining |
| 3 = strong staining | 3 = 11-33% staining |
|  | 4 = 34-66% staining |
|  | 5 = 67-100% staining |

In order to determine statistical differences a K-S and Shapiro-Wilk normality test was performed on flow cytometry data and results were analysed using Mann-Witney test. For tissue sections, the Fisher's exact test was performed whereby tissue sections with a total score above 3 were considered positive.

The results of these statistical analyses, in which $P<0.05$ was considered to be statistically significant, are shown in Table 2.

TABLE 2

| Grade (total patients) | SA44 (GL44) No. of total patients with score more than 2/total no. of patients | SA43 (GL44) No. of total patients with score more than 2/total no. of patients |
|---|---|---|
| I (7) | 7/7 (p = 0.0885) | 6/7 (p = 0.0406) |
| II (9) | 3/9 (p = 0.6372) | 3/9 (p = 1.000) |
| III (10) | 8/10 (p = 0.3498) | 9/10 (p = 0.0055) |
| IV (10) | 8/10 (p = 0.3498) | 8/10 (p = 0.0230) |
| Non-cancerous brain | 5/9 | 2/9 |

EXPERIMENTAL RESULTS 2

The study described above was expanded by the addition of 3 further non-cancerous and 5 further grade II glioma patient tissue samples, to give a cohort as follows:

12 samples of non-cancerous brain,
7 samples of Grade I gliomas,
14 samples of Grade II gliomas,
10 samples of Grade III gliomas, and
10 samples of Grade IV gliomas.

Statistical analysis of this expanded cohort provided further clarification of the ability of the aptamers of the invention to distinguish between non-cancerous brain or samples from Grade I-IV gliomas as set out in Table 3.

TABLE 3

| Grade (total patients) | SA44 (GL44) No. of total patients with score more than 2/total no. of patients | SA43 (GL43) No. of total patients with score more than 2/total no. of patients |
| --- | --- | --- |
| I (7) | 7/7 (p = 0.2451) | 6/7 (p = 0.0063) |
| II (14) | 8/14 (p = 0.7015) | 8/14 (p = 0.0511) |
| III (10) | 8/10 (p = 0.6462) | 9/10 (p = 0.0019) |
| IV (10) | 8/10 (p = 0.6462) | 8/10 (p = 0.0083) |
| Non-cancerous brain | 5/12 | 2/12 |

Figure 6:
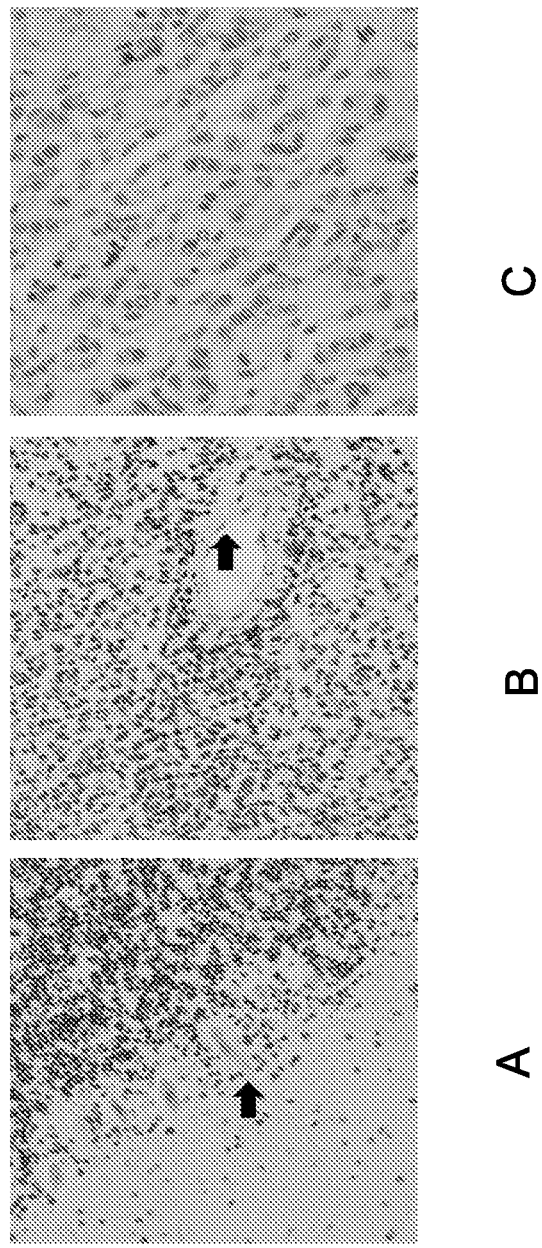
FIG. 6 illustrates that cellular binding of the aptamer of SEQ ID NO: 2 (GL43) is specific for gial and neuronal cells.

FIG. 6 illustrates that cellular binding of the aptamer of SEQ ID NO: 2 (GL43) is specific for gial and neuronal cells. As shown, this aptamers does not label Purkinje cells (unlabelled in Panel A), endothelial cells (Panel B), or meningioma cells (Panel C) in tissue samples.

EXPERIMENTAL RESULTS 3

The ligands bound by the aptamers of the invention were investigated as follows.

Cells of two human glioma cell lines (1321N1: grade II astrocytoma; and U87MG: grade IV glioblastoma), as referred to before, were cultured, and then lysed to obtain extracts of the proteins they expressed.

Samples of these extracts were then incubated with either the aptamer of SEQ ID NO: 2 or the aptamer of SEQ ID NO: 1, in conditions allowing the aptamers to bind their corresponding ligands. Labelled beads capable of binding to the aptamers were then added to this incubation mixture.

The beads, aptamers, and ligands bound to the aptamers were then allowed to precipitate and collected (referred to as the "immunoprecipitate" "IP"). The supernatant, containing non-bound proteins of the extracts was also retained (referred to as the "input").

Immunoprecipitates and inputs were then individually processed and the proteins separated by SDS polyacrylamide gel electrophoresis (SDS-PAGE). Gels were stained using Coomassie blue to allow visualisation of the protein bands. Images of exemplary stained gels are shown in FIGS. 7 and 8.

Portions of the gels containing bands comprising proteins that had been isolated from the extracts by immunoprecipitation were then excised and processed to allow further analysis of the proteins present by mass spectroscopy. Illustrative examples of the areas removed for further investigation are shown in FIGS. 7 and 8.

Figure 7:
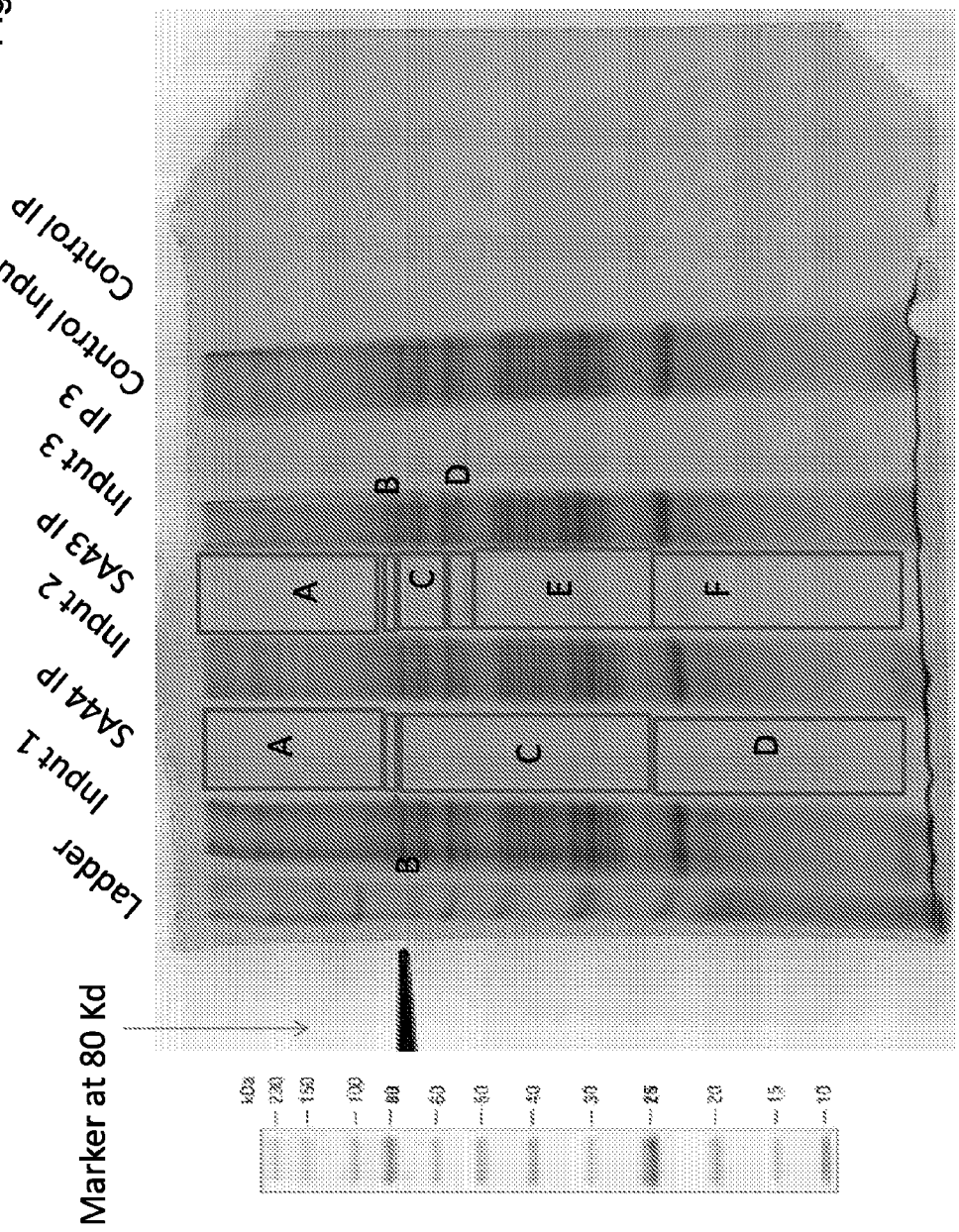
FIG. 7 shows an image of a stained SDS-PAGE gel on which proteins from U87 cells have been separated. Lanes labelled SA44IP and SA43IP contain proteins isolated by immunoprecipitation (IP—more properly referred to as aptamerprecipitation, AP, since antibodies are not used) using aptamers of the invention.
Figure 8:
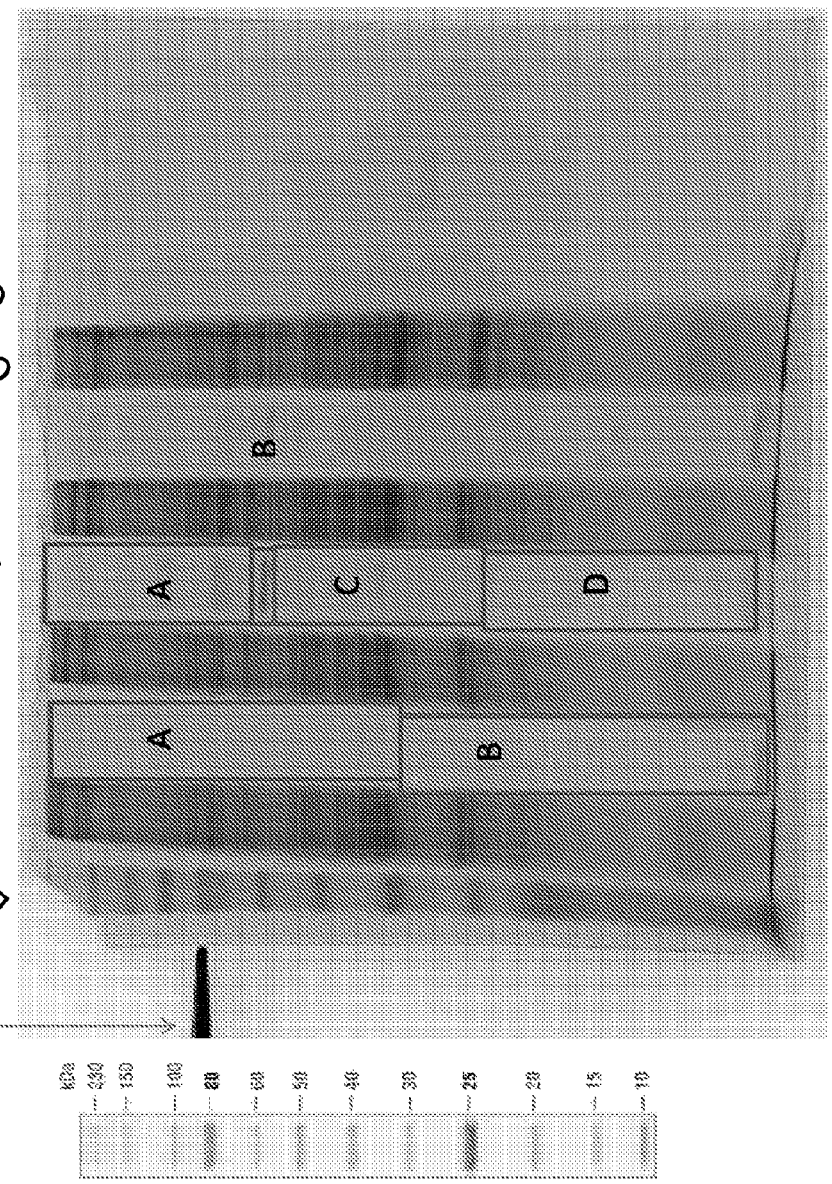
FIG. 8 shows an image of a stained SDS-PAGE gel on which proteins from 1321N1 cells have been separated. Lanes labelled SA44IP and SA43IP contain proteins isolated by immunoprecipitation (IP—more properly referred to as aptamerprecipitation, AP, since antibodies are not used) using aptamers of the invention.
Figure 9:
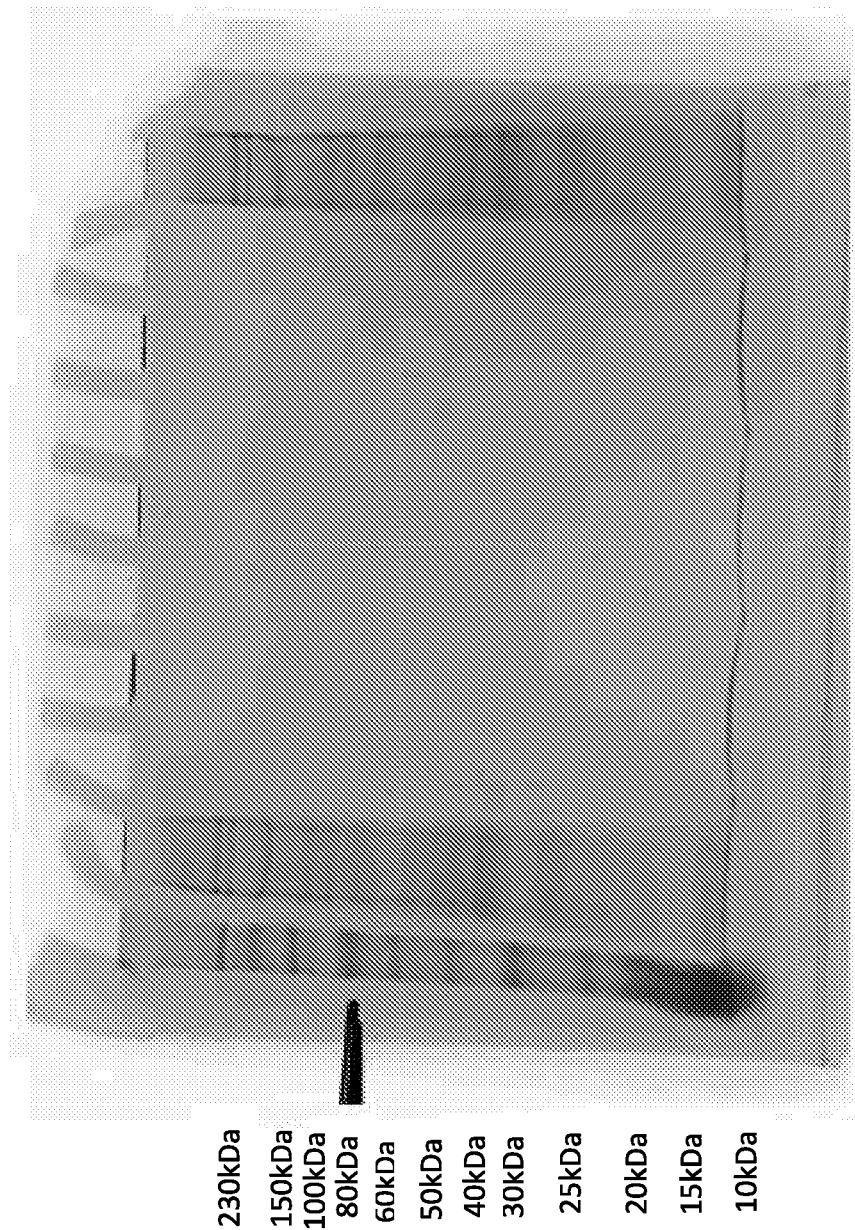
FIG. 9 shows an image of a stained SDS-PAGE gel on which proteins from cells of the Grade IV glioblastoma multiforme primary cell line 9114 have been separated. Lanes labelled SA44AP and SA43AP contain proteins isolated by aptamerprecipitation (AP) using aptamers of the invention.
Figure 10:
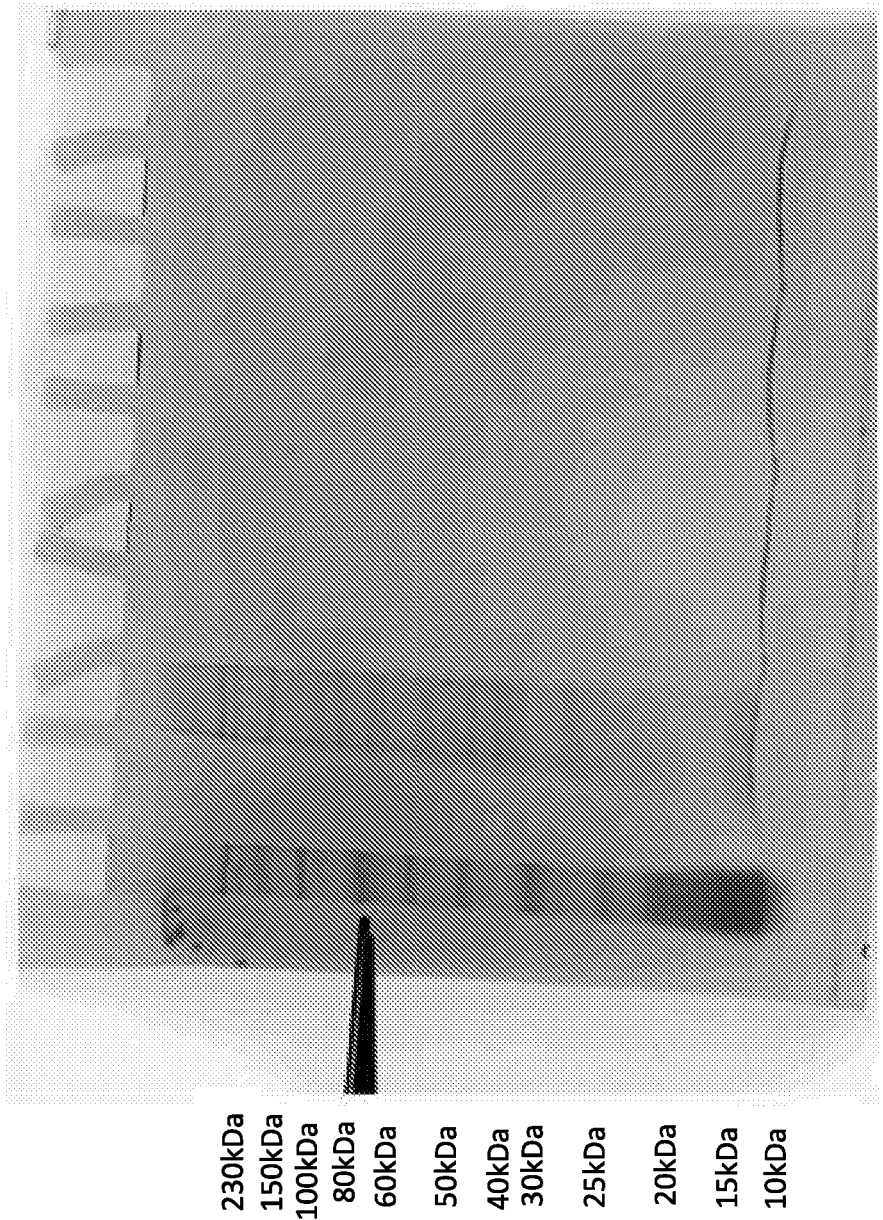
FIG. 10 shows an image of a stained SDS-PAGE gel on which proteins from cells of the Grade IV glioblastoma multiforme primary cell line 9111 have been separated. Lanes labelled SA44AP and SA43AP contain proteins isolated by aptamerprecipitation (AP) using aptamers of the invention.

In these FIG. 7, "SA44IP" and "SA43IP" respectively denote the lanes containing immunoprecipitates produce on incubation with the aptamers of SEQ ID NO: 1 and SEQ ID NO: 2. Lanes labelled "Input 1" and "Input 2" contained proteins from the corresponding supernatants remaining after immunoprecipitation.

Figure 11:
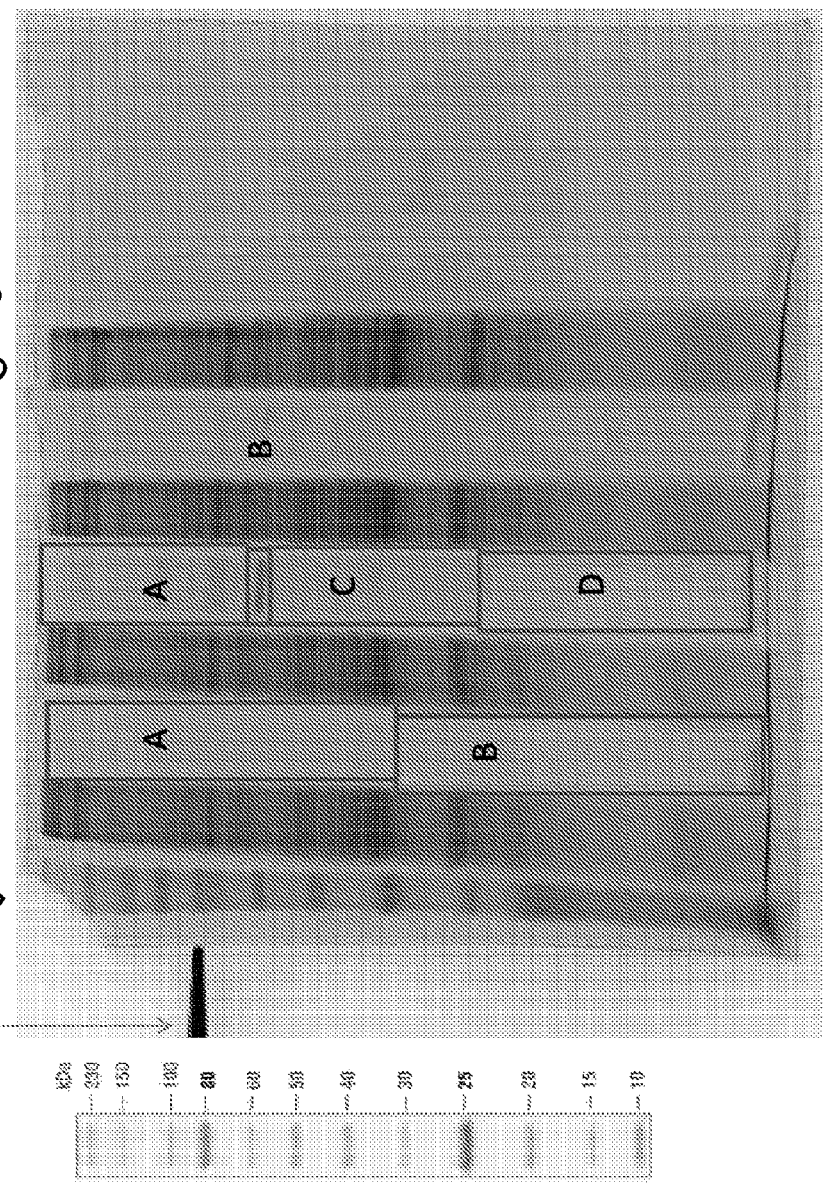
FIG. 11 illustrates the top five significant protein hits from areas of the gel shown in FIG. 7 that have been analysed by mass spectroscopy.
Figure 12:
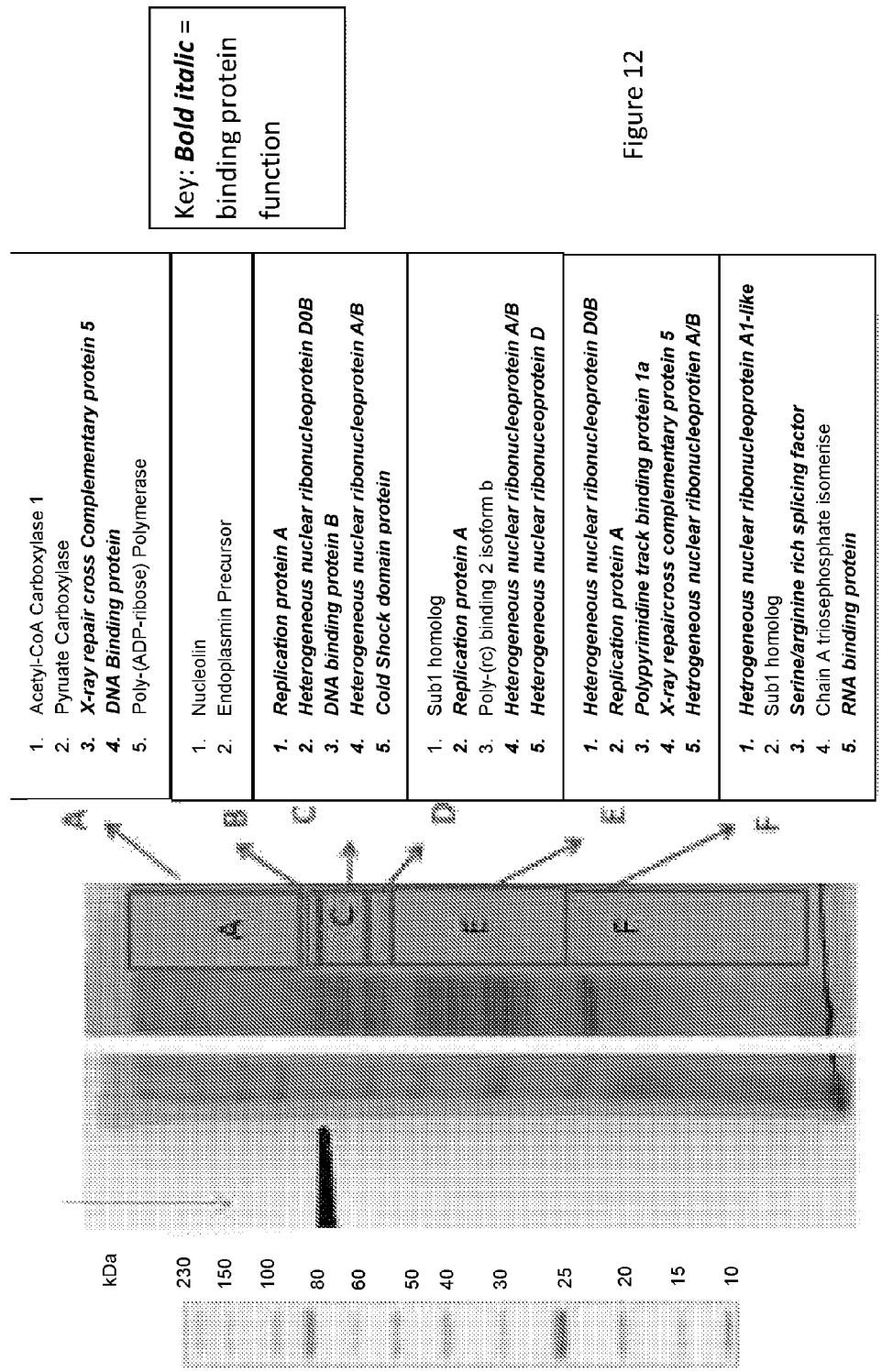
FIG. 12 illustrates the top five significant protein hits from areas of the gel shown in FIG. 8 that have been analysed by mass spectroscopy.

Results produce by the mass spectroscopy analysis are illustrated in FIGS. 11 and 12. Here, details are provided of the top five significant proteins identified in each of the areas of the gel analysed further by mass spectroscopy. The proteins identified are known to form or be associated with the Ku heterodimer, thus identifying the members of this heterodimer (Ku70 and/or Ku80) as the ligand for aptamer SA43 (SEQ ID NO: 2).

Data for the corresponding analysis of the ligands bound by aptamer SA44 (SEQ ID NO: 1) are not shown.

CONCLUSIONS AND FURTHER RESEARCH

Aptamers of the invention, particularly SA44 and SA43 (also designated GL44 and GL43) aptamers, showed significant difference ($p<0.05$) in binding selectivity towards U87Mg cells compared to SVGp12 cells.

SA43 (GL43) aptamer showed significant difference ($p<0.05$) in binding selectivity towards grade I, III and IV glioma tissues compared to the non-cancerous brain tissues.

Future studies will include co-localisation of SA43 (GL43) aptamer with different biomarkers such as GFAP and CD31 to confirm their localisation in the tissue sections.

Future studies will also include generating an aptamer against grade II gliomas.

Drug conjugated with an aptamer will be studied to explore the possible applications in targeted delivery of drug to cancer cells.

Sequence Information

| SEQ ID NO. | Also designated | Sequence |
| --- | --- | --- |
| 1 | SA44 or GL44 | ACG UUA CUC UUG CAA CAC CCA AAC UUU AAU AGC CUC UUA UAG UUC |
| 2 | SA43 or GL43 | ACG UUA CUC UUG CAA CAC AAA CUU UAA UAG CCU CUU AUA GUU C |
| 3 | SA56 or GL56 | UGA UUU UGC AGC ACU UCU UGU UAU CUU AAC GAA CUG UUG AUG A |
| 4 | CL44 | GGAAAAUUAUACCCUCCAUUAAAUCCACCAU UACCACACCCUUUA |
| 5 | U87TDM1 | GTAGGGACTTAGCTCTCACCGTATGGCATGC GTAGTACTGAGAGTGTGGG |
| 6 | U87TDM2 | CACTCCAAAACTCACCTGAACTGTAATAGGG GATGTGTGCTACACTATCG |
| 7 | U87TDM3 | GGCACATTCCGACACGGGTTGGCGGTTTGGG ATTGATGAACTGGCAGTTG |
| 8 | U87TDM6 | GCGTATCGACCACAAACAATAAGGTTACCTG ATCTAGTACGGGTTGTTT |
| 9 | U87TDM7 | GCGGCAGCTGTGCCCGTGCTGCGTCTAGACT CGTGATGAGAAGGAGGGCT |
| 10 | U87TDM9 | CGCTCATTCGTGGATGATTAATGCGGAGCGT GGTGGGAAGCGGGCAGCGG |
| 11 | U87TDM10 | CCGCTAGTGGGCGGACGATGCGTGGGATAGG GGGGCGAATTGGGGGATTT |
| 12 | Neg aptamer | CCG UUA AUU AGG CCC UUA AAU GGC AUA AAA UUU GAA AGG GAA U |

A note on nomenclature used: the aptamers of the invention of SEQ ID NOS: 1, 2, and 3 were originally referred to as GL44, GL43, and GL56 respectively. The inventors then determined that these same designations had previously been applied by others to different aptamers (i.e. aptamers that did not share the sequences set out above), and so the aptamers of SEQ ID NOS: 1, 2, and 3 have subsequently (and preferably) been referred to as SA44, SA43, and SA56 respectively, in order to avoid confusion.

The invention claimed is:

1. An aptamer, comprising a nucleic acid sequence selected from the group consisting of: SEQ ID NO: 6; SEQ ID NO: 7; SEQ ID NO: 8; SEQ ID NO: 9; SEQ ID NO: 10; and SEQ ID NO: 11 or a ligand-binding fragment of the aptamer.

2. An aptamer according to claim 1, or a ligand-binding fragment thereof, in association with an anti-cancer agent.

3. An aptamer according to claim 2, or a ligand-binding fragment thereof, wherein the aptamer, or ligand-binding fragment, and the anti-cancer agent are conjugated with one another.

4. An aptamer according to claim 2, wherein the aptamer and anti-cancer agent are indirectly associated with one another.

5. An aptamer according to claim 4, wherein the anti-cancer agent is associated with a carrier selected from the group consisting of a nanoparticle, and a dendrimer.

6. An aptamer according to claim 2, or a ligand-binding fragment thereof, wherein the anti-cancer agent is selected from the group consisting of a radionuclide, a nanoparticle, a nanocage, a gene silencing agent, and a cytotoxic chemical.

7. An aptamer according to claim 6, wherein the gene silencing agent is selected from the group consisting of an siRNA molecule, a ribozyme, and an antisense oligonucleotide.

8. An aptamer according to claim 7, wherein the gene silencing agent prevents or inhibits expression of Ky70, Ku80, or both Ky70 and Ku80.

9. An aptamer according to claim 1, or ligand-binding fragment thereof, in association with a detection moiety.

10. An aptamer according to claim 9, or a ligand-binding fragment thereof, wherein the detection moiety is selected from the group consisting of a radionuclide, a dye, a fluorophore, a nanoparticle, a nanocage and a chromogenic agent.

11. An aptamer according to claim 1, consisting of a nucleic acid sequence selected from the group consisting of: SEQ ID NO: 6; SEQ ID NO: 7; SEQ ID NO: 8; SEQ ID NO: 9; SEQ ID NO: 10; and SEQ ID NO: 11.

12. A ligand-binding fragment of an aptamer according to claim 1, wherein the fragment retains the capacity to bind to a ligand associated with cancer cells.

13. A pharmaceutical composition comprising an aptamer according to claim 1, or a ligand-binding fragment thereof, and a pharmaceutically acceptable excipient.

14. A pharmaceutical composition according to claim 13, formulated to provide a therapeutically effective amount of the aptamer in a dosage unit of the pharmaceutical composition.

15. A pharmaceutical composition according to claim 13, wherein the aptamer is in association with an anti-cancer agent and wherein the composition is formulated to provide a therapeutically effective amount of the anti-cancer agent associated with the aptamer.

16. A method of treating cancer in a subject, the method comprising administering to a subject in need thereof a therapeutically effective amount of a pharmaceutical composition according to claim 13.

17. A method of treating cancer in a subject, the method comprising administering to a subject in need thereof a therapeutically effective amount of an aptamer according to claim 1, or a ligand-binding fragment thereof.

18. An oligonucleotide sharing at least 75% sequence identity with any one of SEQ ID NOS: 6 to 11.

19. An oligonucleotide according to claim 18 sharing at least 95% sequence identity with any one of SEQ ID NOS: 6 to 11, wherein the oligonucleotide retains the same binding profile as the aptamer of SEQ ID NOS: 6 to 11.

20. An aptamer according to claim 6, or a ligand-binding fragment thereof, wherein the nanoparticle comprises a nanoshell.

21. An aptamer according to claim 10, or a ligand-binding fragment thereof, wherein the nanoparticle comprises a nanoshell.

22. A method according to claim 16, wherein the cancer is brain cancer.

23. A method according to claim 22, wherein the brain cancer is selected from the group consisting of gliomas, meningiomas, pituitary adenomas, and nerve sheath tumors.

24. A method according to claim 22, wherein the brain cancer is a glioma.

25. A method according to claim 16, wherein the aptamer is in association with the anti-cancer agent and wherein the composition is formulated to provide a therapeutically amount of the anti-cancer agent associated with the aptamer.

26. A method according to claim 25, wherein the aptamer and the anti-cancer agent are directly associated with each other.

27. A method according to claim 25, wherein the aptamer and the anti-cancer agent are indirectly associated with each other.

28. A method according to claim 16, wherein the composition is administered orally.

29. A method according to claim 16, wherein the composition is administered via injection.

* * * * *